United States Patent [19]

Tsai et al.

[11] Patent Number: 5,989,556
[45] Date of Patent: *Nov. 23, 1999

[54] COMPOSITIONS OF MATTER USEFUL IN THE TREATMENT OF VIRAL INFECTIONS DERIVED FROM PLANT EXTRACTS

[75] Inventors: Hsiu-Hsien Tsai, Chang-Huah, Taiwan; Shie-Ming Hwang, Columbus, Ohio

[73] Assignee: Sage R&D, Columbus, Ohio

[*] Notice: This patent is subject to a terminal disclaimer.

[21] Appl. No.: 08/890,065

[22] Filed: Jul. 9, 1997

Related U.S. Application Data

[60] Provisional application No. 60/016,100, Jul. 9, 1996, and provisional application No. 60/021,467, Jul. 10, 1996.

[51] Int. Cl.$^6$ ................................................... A61K 35/78
[52] U.S. Cl. ....................... 424/195.1; 426/655; 514/885; 514/894
[58] Field of Search .................. 424/195.1; 514/885, 514/894; 426/655

[56] References Cited

U.S. PATENT DOCUMENTS

| | | | |
|---|---|---|---|
| 4,886,666 | 12/1989 | Liu ....................................... | 424/195.1 |
| 5,178,865 | 1/1993 | Ho et al. .............................. | 424/195.1 |
| 5,366,725 | 11/1994 | Okubo et al. ........................ | 424/85.4 |
| 5,411,733 | 5/1995 | Hozumi et al. ...................... | 424/195.1 |

FOREIGN PATENT DOCUMENTS 1079157  12/1993  China .

OTHER PUBLICATIONS

Ghazanfar, Handbook of Arabian Medicinal Plants, CRC Press, Inc., Boca Raton, FLA, pp. 200–202, 1994.
Kugach et al., Khim–Farm ZH, 22:471–475, English translation of abstract only, 1988.
Kikuchi et al., Yakugaku Zasshi, 101:575–578, 1981, English translation of abstract only, 1981.
Junxian et al., Zhongguo Zhongyao Zazhi, 3:168–170, English translation of abstract only, 1990.
Nakanishi et al., Shoyakugaku Zasshi, 47:295–300, 1993.
Tan et al., J. Nat. Prod., 54:143–154, 1991.
Thorne et al., Antiviral Res., 5:335–343, 1985.
D.S. Chen, *J. Formos. Med. Assoc.*, 95(1), 6–12 (1996).
R. P. Perrillo, *Digestive Diseases and Sciences*, 38(4), 577–593 (1993).
A.S.F. Lok, H. T. Chung, V. W. S. Liu, & O. C. K. Ma, *Gastroenterology*, 105(6), 1833–1838 (1993).
D.S. Chen, *Science*, 262, 369–370 (1993).
N. Terrault & T. Wright, *New Engl. J. Med.*, 332(22), 1509–1511 (1995).
B. Jasny, *Science*, 260(5112), 1219 (1993).
P. Piot, *Science*, 272(5270), 1855 (1996).
M. I. Johnston & D. F. Hoth, *Science*, 260(5112), 1286–1293 (1993).
D. D. Richman, *Science*, 272(5270), 1886–1888 (1996).
R. S. Chang & H. W. Yeung, *Antiviral Research*, 9, 163–175 (1988).

M. Ito et al., *Antiviral Research*, 7, 127–137 (1987).
H. Y. Hsu, Y. P. Chen, & M. Hong, *The Chemical Constituents of Oriental Herbs*, vol. 2, Oriental Healing Arts Institute, Los Angeles, California, U.S.A., 51, 53–55, 142–143, 742, 758–759 (1985).
H. Y. Hsu, Y. P. Chen, S. G. Hsu, J. S. Hsu, C. J. Chen, & H. C. Chang, *Concise Pharmacognosy*, New Medicine Publishing Co., Taipei, Taiwan, R.O.C., 90, 97, 105–106, 117–118, 126–127, 130–131, 133, 144–145, 152–153, 156–157, 161–162, 174, 176–177, 357–358, 381–382, 384–385, 456–457, 577–578 (1985).
H. Y. Hsu, Y. P. Chen, & M. Hong, *The Chemical Constituents of Oriental Herbs*, Oriental Healing Arts Institute, Los Angeles, California, U.S.A., 114–115, 249–250, 1400–1401, 1406 (1982).
C.–J. Chou, L.–C. Lin, S.–Y. Hsu, and C.–F. Chen, *J. Clin. Med.*, 4(2), 143–149 (1993).
C.–W. Chang, M.–T. Lin, S.–S. Lee, K.C.S. Liu, F.–L. Hsu, & J.–Y. Lin, *Antiviral Research*, 27, 367–374 (1995).
P. J. Houghton, Z. Boxu, & Z. Xisheng, *Phytother. Res.*, 7, 384–386 (1993).
J.F. John, R. Kuk, & A. Rosenthal, *Abstr. Gen. Meet. Am. Soc. Microbiol.*, 94, 481 (1994).
K. Yamasaki, T. Otake, H. Mori, M. Morimoto, N. Ueba, Y. Kurokawa, K. Shiota, & T. Yuge, *Yakugaku Zasshi*, 113(11), 818–824 (1993).
X. J. Yao, M. A. Wainberg, & M. A. Parniak, *Virology*, 187(1), 56–62 (1992).
H.D. Tabba, R. S. Chang, & K. M. Smith, *Antiviral Research*, 11, 262–273 (1989).

(List continued on next page.)

*Primary Examiner*—David M. Naff
*Assistant Examiner*—Janet M. Kerr
*Attorney, Agent, or Firm*—Donald O. Nickey; Standley & Gilcrest, LLP

[57] ABSTRACT

Compositions derived from Chinese herbal medicines, medicinal plants and extracts thereof, are provided for the treatment of animals infected with viruses, especially with hepatitis B virus (HBV), hepatitis C virus (HCV), and human immunodeficiency virus (HIV). More specifically, the compositions of the present invention are derived from various Chinese herbal medicines or medicinal plants which have a long history of human consumption. The compositions of the invention are obtained through specific techniques and have demonstrated outstanding efficacy for treating human HBV carriers and hepatitis C patients. Compositions according to the invention have also exhibited in vitro antiviral activities against murine leukemia virus (MuLV) and HIV. HIV is the virus known to cause acquired immunodeficiency syndrome (AIDS) in humans and AIDS presents special problems to the medical community which the present invention addresses. Preferred compositions contain the herbal ingredients AEGINETIAE HERBA, BLECHNI RHIZOMA, LESPEDEZAE HERBA, POLYGONI CUSPIDATI RHIZOMA, FORSYTHIAE FRUCTUS, and LIGUSTRI FRUCTUS, or contain the herbal ingredients AEGINETIAE HERBA, LONICERAE FLOS, PRUNELLAE SPICA, and LESPEDEZAE HERBA.

4 Claims, No Drawings

OTHER PUBLICATIONS

M. Zheng, *J. Tradit. Chin. Med.,* 8(3), 203–206 (1988).

S. Y. Ryu, C.-K. Lee, C. O. Lee, H. S. Kim, & O. P. Zee, *Arch. Pharmacol. Res. (Seoul),* 15(3), 242–245 (1992).

Y. L. Lin, Y. H. Kuo, G. H. Lee, and S. M. Peng, *J. Chem. Research (S),* 320–321 (1987).

T. Nagai, et al., *Chem. Pharm. Bull.,* 38(5), 1329–1332 (1990).

M. Takechi & Y. Tanaka, *Planta Medica,* 42, 69–74 (1981).

C. J. M. Kane, et al, *Bioscience Reports,* 8, 85–94 (1988).

H. C. Chang, *Medicinal Herbs I,* Holiday Publishing Co., Taipei, Taiwan, R.O.C., 15, 36, 100, 113, 127, 147 (1990) (No translation).

H. C. Chang, *Medicinal Herbs I,* Holiday Publishing Co., Taipei, Taiwan, R.O.C., 15, 131, 135, 155 (1991). (No. translation).

W. S. Kan, *Pharmaceutical Botany,* National Research Institute of Chinese Medicine, Taipei, Taiwan, R.O.C., 113, 124–130, 200–201, 206–207, 289–290, 353–354, 442–444, 485, 487–488, 497, 505, 513–514, 522, 527–529, 558, 562–563, 648–649 (1971). (No translation).

M. S. Lee, *Frequently Used Chinese Crude Drugs and Folk Medicines Handbook,* 12th Ed., Sheng–Chang Medicinal Record Magazine Publishing Co., Taipei, Taiwan, R.O.C., 4–6, 17, 21, 29, 36, 38, 40, 48, 64, 71, 79, 85 (1992). (No translation).

*Instruction of "Taifu" Serodia–HBs Test Reagent for HBsAg Detection,* Taifu Pharmaceutical Co., Ltd., Taoyuan, Taiwan, R.O.C.

D. S. Chen & J. L. Sung, *J. Formosan Med. Assoc.,* 77, 263–270 (1978).

T. Juji & T. Yokochi, Japan, *J. Exp. Med.,* 39, 615–620 (1969).

T. Mosmann, *J. Immunological Methods,* 65, 55–63 (1983).

H. Ruebsamen–Waigmann, et al., *J. Med. Virology,* 19, 335–344 (1986).

Ch. Mueller, et al., *Fresenius Z. Anal. Chem.,* 330, 352–353 (1988).

H. V. Briesen, et al., *J. Med. Virology,* 23, 51–66 (1987).

*Instruction of Kyokuto TA–E Transaminase Assay Reagents,* Permit No. (62AM)0885, Kyokuto Pharmaceutical Industry Co., Ltd., Tokyo, Japan, 1994.

*Instruction of Yatrozyme TA–Lq Transaminase–assay Reagent Solution (Enzyme Assay),* Commodity No. 817245 (RM163–K), Yatron Co., Ltd., Diayatron Co., Ltd., Tokyo, Japan.

U. Lippi & G. Guidi, *Clin. Chim. Acta.,* 28, 431–437 (1970).

COMPOSITIONS OF MATTER USEFUL IN THE TREATMENT OF VIRAL INFECTIONS DERIVED FROM PLANT EXTRACTS

RELATED APPLICATIONS

This application claims priority to a provisional application filed Jul. 9, 1996, Ser. No. 60/016,100 entitled: ANTI-VIRAL AGENTS; and to a provisional application filed Jul. 10, 1996, Ser. No. 60/021,467 entitled: ANTI-VIRAL AGENTS FROM CHINESE MEDICINAL HERBS.

TECHNICAL FIELD

This invention relates to compositions of matter comprising the antiviral active components derived from Chinese herbal medicines, medicinal plants and extracts thereof, and to their use for the treatment of humans or animals infected with viruses, especially with hepatitis B virus (HBV), hepatitis C virus (HCV), and human immunodeficiency virus (HIV). More specifically, the compositions of matter of the present invention are derived from various Chinese herbal medicines or medicinal plants which have a long history of human consumption. The compositions of matter of the invention are obtained through specific techniques and have demonstrated outstanding efficacy for treating human HBV carriers and hepatitis C patients. The compositions of matter according to the invention have also exhibited in vitro antiviral activities against murine leukemia virus (MuLV) and HIV. HIV is the virus known to cause acquired immunodeficiency syndrome (AIDS) in humans and AIDS presents special problems to the medical community which the present invention addresses. The active principles of the individual antiviral active herbal medicines or medicinal plants or extracts thereof have been isolated through specific isolation techniques and have been characterized through the use of accepted chemical techniques.

BACKGROUND

Modern medical science is constantly searching for new and more powerful agents to prevent, treat or retard bacterial and viral infections and cure the diseases they cause. Bacterial and viral infections of humans and domestic animals cost billions of dollars annually. Vast sums of money are spent each year by pharmaceutical companies to identify, characterize, and produce new antibiotics and antivirals to combat the emerging drug resistant strains which have become a serious problem. Reliable prophylactic treatments for disease prevention are also of major interest. Yet, despite the costs and efforts to identify treatments for viral infections, such as hepatitis and AIDS, effective therapies remain elusive.

Hepatitis is a disease of the human liver. It is manifested with inflammation of the liver and is usually caused by viral infections and sometimes from toxic agents. Hepatitis may progress to liver cirrhosis, liver cancer, and eventually death. Several viruses such as hepatitis A, B, C, D, E and G are known to cause various types of viral hepatitis. Among them, HBV and HCV are the most serious. HBV is a DNA virus with a virion size of 42 nm. HCV is a RNA virus with a virion size of 30–60 nm. See D. S. Chen, *J. Formos. Med. Assoc.*, 95(1), 6–12 (1996).

Hepatitis B is a major health problem worldwide, especially in Asia and Africa. Approximately 300 million people are chronically infected with HBV worldwide. More than one million carriers of HBV are found in the United States. HBV infection is currently the main cause of liver cirrhosis and cancer. HBV carriers are not only long-term reservoirs of the virus but also may develop chronic liver disease and have a greatly increased risk of developing liver cirrhosis and cancer. The progression from chronic hepatitis B to cirrhosis is frequently insidious and occurs without a noticeable change in symptoms. Once the symptoms of cirrhosis or cancer are manifested, therapies are of little value.

Prevention of HBV infection is possible through vaccination which is safe and effective. However, vaccination is not effective in treating those already infected, i.e., carriers and patients. Many drugs have been used in treating chronic hepatitis B and none have been proven to be effective, except interferon. Treatment with interferon has limited success and has frequently associated with adverse side effects such as fatigue, fever, chills, headache, myalgias, arthralgias, mild alopecia, psychiatric effects and associated disorders, autoimmune phenomena and associated disorders and thyroid dysfunction. Treatment with interferon for sixteen (16) weeks has been shown to be effective with a sustained loss of viral replication in approximately 40% of hepatitis B patients. The great majority of responders had normal serum aminotransferase levels and relapse rates appeared to be low. See R. P. Perrillo, *Digestive Diseases and Sciences*, 38(4), 577–593 (1993). However, a higher long-term relapse rate (24%) was reported in Chinese patients with chronic hepatitis B who underwent interferon therapy. See A. S. F. Lok, H. T. Chung, V. W. S. Liu, & O. C. K. Ma, *Gastroenterology*, 105(6), 1833–1838 (1993).

Moreover, serum hepatitis B surface antigen (HBsAg) disappeared in 10 to 15% of patients treated with interferon. The loss of HBsAg coincided with the disappearance of HBV. Improvement in liver histology was sustained years later in HBsAg-negative patients. The lack of disease progression could thus conceivably result in the prevention of liver cancer when treatment is provided in the pre-cirrhotic stage of infection. See R. P. Perrillo, *Digestive Diseases and Sciences*, 38(4), 577–593 (1993).

Hepatitis C has been previously described as a non-A non-B hepatitis, which is caused by HCV. There are approximately 100 million HCV carriers worldwide. An estimated 3.5 million people have chronic hepatitis C in the United States. HCV infection will lead to liver cirrhosis and cancer with less clinical manifestation. Most hepatitis C patients do not have particular symptoms and can thus be easily overlooked until it is too late for therapy. This poses a potentially more serious problem than hepatitis B. HCV carriers also become long-term reservoirs of the virus and eventually develop chronic liver disease and have a greatly increased risk of developing liver cirrhosis and cancer. See D. S. Chen, *Science*, 262, 369–370 (1993).

No effective immunization is currently available, and hepatitis C can only be controlled by preventive measures such as improvement in hygiene and sanitary conditions and interrupting the route of transmission. At present, the only acceptable treatment for chronic hepatitis C is interferon which requires at least six (6) months of treatment. Initial treatment has a response rate of about 50%. However, half of those responding relapse after cessation of interferon treatment. Therefore, only about 25% of patients have a sustained response. See D. S. Chen, *J. Formos. Med Assoc.*, 95(1), 6–12 (1996) and N. Terrault & T. Wright, *New Engl. J. Med.*, 332(22), 1509–1511 (1995). Because the interferon therapy has limited efficacy and frequent adverse effects, a more effective regimen is needed.

AIDS is a deadly disease caused by HIV. It has been plaguing the world since the first description of the disease in 1981 and the discovery of its causative agent, HIV, in 1983. About 13 million people were infected with HIV worldwide in 1993 and the number has increased to about 21 million in 1996. See B. Jasny, *Science*, 260(5112), 1219 (1993) and P. Piot, *Science*, 272(5270), 1855 (1996).

Several drugs have been approved for treatment of this devastating disease, such as azidovudine (AZT), didanosine (dideoxyinosine, ddI), d4T, zalcitabine (dideoxycytosine, ddC), nevirapine, lamivudine (epivir, 3TC), saquinavir (Invirase), ritonavir (Norvir), indinavir (Crixivan), and delavirdine (Rescriptor). See M. I. Johnston & D. F. Hoth, *Science*, 260(5112), 1286–1293 (1993) and D. D. Richman, *Science*, 272(5270), 1886–1888 (1996

All drugs currently approved for AIDS treatment utilize inhibition of viral proliferation and are viral reverse transcriptase inhibitors or viral protease inhibitors. More protease inhibitors, such as nelfinavir and improved saquinavir, are in development. An AIDS vaccine (Salk's vaccine) has been tested and several proteins which are chemokines from CD8 have been discovered to act as HIV suppressors.

In addition to the above synthetic nucleoside analogs, proteins, and antibodies, several plants and substances derived from plants have been found to have in vitro anti-HIV activity, such as *Lonicera japonica* and *Prunella vulgaris*, and glycyrrhizin from *Glycyrrhiza radix*. See R. S. Chang & H. W. Yeung, *Antiviral Research*, 9, 163–175 (1988) and M. Ito, et al., *Antiviral Research*, 7, 127–137 (1987).

Despite all of the available pharmaceuticals for the treatment of HIV, there is still no cure for the deadly disease. HIV viruses continue to mutate and become resistant to existing drugs such as the reverse transcriptase and protease inhibitors. Recently, a therapy of using two (2) or three (3) anti-HIV drugs in combination has been found effective in significantly lowering the HIV loads in AIDS patients. The results have been promising. However, the virus continues to develop resistance to the drugs and the long-term outcome (survival and cure rates) is still unknown. Thus, the medical communities throughout the world continue to search for drugs that can prevent the HIV infections, treat the HIV carriers to prevent them from progressing to full-blown deadly AIDS, and treat the AIDS patients.

Herbal Medicines

The use of herbal drugs and folk medicines have been known for thousands of years in China. These herbal approaches to the treatment of numerous illnesses, from arthritis to viral infections, have been previously viewed by western medicine as ineffective and dangerous. During the 19th century, many home remedies containing herbs were patented and sold. Modern drugs have replaced those remedies, but many modern drugs contain ingredients derived from herbs. For example, in 1776 the English botanist and physician William Withering learned that an herbal tea made by an old farm woman was effective in treating dropsy, or excess water in the tissues, which is caused by the inability of the heart to pump strongly enough. He found that one ingredient of the tea, which was made from leaves of the foxglove plant, strengthened the heart's pumping ability. The drug made from the foxglove plant is now known as digitalis.

Folk medicine is a relatively modern term to the West and has come to mean the care and treatment of the sick through a variety of herbal medicines. In recent years, folk medicines have become of increasing interest to many people in the western scientific medical community.

Prior Art—Herbal Medicines

A Chinese herbal medicine known as AEGINETIAE HERBA (a.k.a., GOLDEN LOCK KEY or LOTUS HERBA); has traditionally been used to treat illnesses such as swollen and sore throat, urinary tract infection, osteomyelitis, boil, tonsillitis, goiter, pharyngitis, thyroiditis, enteritis, liver disease, cancer, rheumatism, hematemesis, neurasthenia, eye redness, piles, menstruation irregularity, dropsy, jaundice, hernia, snake bite, and child developmental retardation. AEGINETIAE HERBA is prepared from the dried whole plant of *Aeginelia indica* which belongs to the family of Orobanchaceae. *Dichondra micrantha, Striga lutea* and *Dichondra repens* are also used to prepare this herbal medicine. Treatment dosage using the dried plant is typically from 4 to 150 g per day. It should be noted that the plant tastes bitter and is toxic.

Okubo et al. disclose that a phosphate buffered saline (PBS) extract (pH 7.2 at ambient to 4° C.) from the seeds of *Aeginetia indica* exhibits excellent carcinostatic effect and possesses interleukin-2 and interferon-γ inducing potency. The PBS was a 0.1 M phosphate buffered physiological saline at pH 7.2, not containing calcium or magnesium ions. The extracted substance is taught to be a macromolecular polysaccharide which may or may not contain lipid A binding with protein depending on whether the extraction is conducted using butanol or phenol. The extracted substance was soluble in water and insoluble in n-butanol. Its molecular weight was within the range of 100,000 to 200,000 dalton. See S. Okubo, M. Sato, & K. Himeno, U.S. Pat. No. 5,366,725, issued on Nov. 22, 1994.

A Chinese herbal medicine known as BAPHICA-CANTHIS RHIZOMA ET RADIX has traditionally been used to treat numerous illnesses such as fever, abscess, erysipelas, swollen sore throat, headache, jaundice, plague, leucorrhea, and syphilis. BAPHITCACANTHIS RHIZOMA ET RADIX is prepared from the dried rhizoma and root of *Baphicacanthes cusia, Strobilanthes cusia, Isatis tinctoria, Isatis indigotica*, or *Polygonum tinctorium*. It has been reported that this herbal medicine has exhibited inhibition of flu virus in vitro. A decoction from boiling the root of *Isatis tinctoria* in water has also exhibited antibacterial effect. *Baphicacanthes cusia* and *Strobilanthes cusia* belong to the family of Acanthaceae. *Isatis tinctoria* and *Isatis indigotica* belong to the family of Cruciferae. *Polygonum tinctorium* belongs to the family of Polygonaceae. Treatment doses are typically 10 to 19 g per day for BAPHICA-CANTHIS RHIZOMA ET RADIX.

Ho et al. disclose the use of an extract from a mixture of herbs including *Isatis tinctoria* for the in vitro inhibition of HIV infection in human T lymphocyte cells and mononuclear phagocytic lineage cells. The activity was based on the test results of a water extract from a mixture of three herbs: *Isatis tinctoria* (or *Isatis indigotica*), *Lonicera japonica*, and *Polygonum bistorta*. See D. D. Ho & X. S. Li, U.S. Pat. No. 5,178,865, issued on Jan. 12, 1993.

A compound known as tryptanthrin has been identified as the principal antifungal agent in the leaf of *Strobilanthes cusia* and as the main antidermatophytic substance in the leaf of *Polygonum tinctorium* and *Isatis tinctoria*. See H. Y. Hsu, Y. P. Chen, & M. Hong, *The Chemical Constituents Of Oriental Herbs*, Vol. 2, Oriental Healing Arts Institute, Los Angeles, Calif., U.S.A., 758–759 (1985).

The Chinese herbal medicine known as BLECHNI RHIZOMA, which is also known as DRYOPTERIS CRASSIRHIZOMAE RHIZOMA has traditionally been used to treat illnesses such as cut injury, swelling, fever, measles and erysipelas. BLECHNI RHIZOMA is prepared from the dried root and stem of *Blechnum orientate* which belongs to the family of Polypodiaceae or Blechnaceae. DRYOPTERIS CRASSIRHIZOMAE RHIZOMA is prepared from the dried root and stem of *Dryopteris crassirhizoma* which belongs to the family of Aspidiaceae. *Osmunda japonica* (Osmundaceae family), *Woodwardia orientalis* and *Woodwardia unigemmata* (Blechnaceae family), *Athyrium acrostichoides* (Aspidiaceae or Athyriaceae family), *Sphaeropteris lepifera* (Cyatheaceae family), *Cyrtomium falcatum*, and *Cyrtomium fortunei* (Aspidiaceae family) have also been used for preparation of these herbal medicines. These herbal medicines taste bitter and astringent and are slightly toxic. Treatment dosages are typically 4 to 11 g per day.

*Blechnum orientate* has also shown a strong inhibition effect against the influenza virus. Filmarone, filicin, aspidin, albaspidin, and filicic acid which are found in *Dryopteris crassirhizoma* have been characterized as having an anthelmintic effect. See H. Y. Hsu, Y. P. Chen, S. G. Hsu, J. S. Hsu, C. J. Chen, & H. C. Chang, *Concise Pharmacognosy*, New Medicine Publishing Co., Taipei, R.O.C., 577–578 (1985); and H. Y. Hsu, Y. P. Chen, & M. Hong, *The Chemical Constituents Of Oriental Herbs*, Oriental Healing Arts Institute, Los Angeles, Calif., U.S.A., 249–250 (1982).

Hozumi et al. disclose the rhizome of *Dryopteris crassirhizoma* as an antiherpesviral agent, antipolioviral agent, and anti-varicella-zoster virus agent. The rhizome of *Cyrtomium fortunei* and the rhizome of *Woodwardia orientalis* are also disclosed as antiherpesviral, antipolioviral, anti-measles virus, anti-varicella-zoster virus, and anti-cytomegalovirus (CMV) agents, as well as an anti-DNA and anti-RNA virus agent. See T. Hozumi, T. Matsumoto, H. Ooyama, T. Namba, K. Shiraki, M. Hattori, M. Kurokawa, & S. Kadota, U.S. Pat. No. 5,411,733, issued May 2, 1995.

A Chinese herbal medicine known as BLETILLAE TUBER has traditionally been used to treat illnesses such as hemoptysis, epistaxis, hematemesis, abscess, burn, dry and chapped skin, tuberculosis, gastric ulcer, and sores. BLETILLAE TUBER has astringent, antibacterial and antifungal properties. BLETILLAE TUBER is prepared from the dried tuber of *Bletilla striata* which belongs to the family of Orchidaceae. BLETILLAE TUBER tastes bittersweet, astringent and is nontoxic. Treatment dose is typically 2 to 11 g per day for an average human.

Chinese herbal medicines known as CIRSII RHIZOMA ET RADIX and BREEAE RADIX have traditionally been used to treat illnesses such as hematemesis, acute infectious hepatitis, cut bleeding, sores, and abscess. CIRSII RHIZOMA ET RADIX is prepared from the dried rhizoma or root or the whole plant of plants such as *Cirsium japonicum*, *Cirsium albescens*, and *Cirsium japonicum* var. australe which are from the Compositae family. BREEAE RADIX is prepared from the dried root of Compositae family plants such as *Breea segetum* (also known as *Cephalanoplos segetum*) and *Breea setosum*. Both herbal medicines taste sweet and slightly bitter, and are nontoxic. Treatment dose is typically 5 to 75 g per day for the average human.

A Chinese herbal medicine known as DICHONDRAE HERBA has traditionally been used to treat illnesses such as jaundice, dysentery, gonorrhea, dropsy, swollen boil, convulsion, encephalitis, rheumatism, hernia, diabetes mellitus, and hypertension. DICHONDRAE HERBA is prepared from the dried whole plant of *Dichondra repens* or *Dichondra micrantha* which belongs to the family of Convolvulaceae. The plant tastes bitter and is nontoxic. Treatment dosage of the dried plant is typically 10 to 40 g per day. Nine (9) compounds which were isolated from n-hexane and ethanol extracts of the whole herb of *Dichondra micrantha* have been identified. These compounds are maltol, umbelliferone, scopoletin, umbelliferone-7-O-glucopyranoside, scopolin, astragalin, isoquercitrin, kaempferol-3-O-rutinoside, and quercetin-3-O-rutinoside. See C.-J. Chou, L.-C. Lin, S.-Y. Hsu and C.-F. Chen, *J. Chin. Med.*, 4(2), 143–149 (1993).

A Chinese herbal medicine known as FORSYTHIAE FRUCTUS has traditionally been used to treat illnesses such as sores, abscess, lymph node swelling, urethritis, and hypertension. It was also found to inhibit several bacteria and influenza virus. FORSYTHIAE FRUCTUS is prepared from the dried mature fruit of *Forsythia suspensa*, *Forsythia viridissima*, or *Forsythia koreana* which belong to the family Oleaceae. The herbal medicine tastes bitter and is nontoxic. Treatment dosage is typically 3 to 11 g per day.

Hozumi et al. disclose that the fruit of *Forsythia suspensa* is an antipolioviral agent and an anti-measles virus agent useful in treating these viral infections. See T. Hozumi, T. Matsumoto, H. Ooyama, T. Namba, K. Shiraki, M. Hattori, M. Kurokawa, & S. Kadota, U.S. Pat. No. 5,411,733, issued May 2, 1995.

The compounds forsythoside A (found in the leaf of *Forsythia suspensa*), forsythoside B (found in the stem of *Forsythia koreana*), and forsythoside C and forsythoside D (found in the fruit of *Forsythia suspensa*) have been reported to exhibit antibacterial activity against *Staphylococcus aureus* at a concentration less than 2 mM. Suspensaside (found in the fruit of *Forsythia suspensa*, likely the same as forsythoside C) has also been reported to exhibit antibacterial activity against *Staphylococcus aureus Terashima* with a minimum inhibition concentration (MIC) of 2.6 mg/mL. See H. Y. Hsu, T. P. Chen & M. Hong, *The Chemical Constituents of Oriental Herbs*, Vol. 2, Oriental Healing Arts Institute, Los Angeles, Calif., U.S.A., 53–55, 142–143 (1985).

A Chinese herbal medicine known as HEDYOTIS (also known as OLDENLANDIAE HERBA) has traditionally been used to treat illnesses such as urethra infection, pharyngitis, laryngitis, tonsillitis, subacute or chronic coccygodynia, appendicitis, intestinal cancer, contusion injury and eye disease. It has also been found to have weak antibacterial activity in vitro. HEDYOTIS is prepared from the dried whole plant of *Hedyotis diffusa* (also known as *Oldenlandia diffusa*) which belongs to the family Rubiaceae. The herbal medicine tastes sweet and is nontoxic. Treatment dosage is typically 19 to 300 g per day.

The Chinese herbal medicines known as LESPEDEZAE HERBA and SENECINIS HERBA have traditionally been used to treat illnesses such as urine incontinence, gonorrhea, asthma, stomach ache, general weakening and exhaustion, diarrhea, contusion injury, eye disease, eye redness, renal disease, acute inflammatory disease, cataract, dysentery, enteritis, jaundice, flu, septicemia, sore, swelling, and a disease of the palm. LESPEDEZAE HERBA is prepared from the dried whole plant of *Lespedeza cuneata* which belongs to the family Leguminosae. SENECINIS HERBA is prepared from the dried whole plant of *Senecio scandens* which belongs to the family Compositae. The extracts of *Lespedeza cuneata* and *Senecio scandens* have been shown to have an antibacterial effect. Both herbs taste sour, astringent and bitter. Treatment dose is typically 4 to 40 g per day.

A Chinese herbal medicine known as LIGUSTRI FRUCTUS has traditionally been used as a tonic and to treat illnesses such as insomnia, constipation, early white hair, neck lymph nodes tuberculosis and dropsy. LIGUSTRI FRUCTUS is prepared from the dried mature fruit of *Ligustrum lucidum* or *Ligustrum japonicum* which belongs to the family Oleaceae. The leaves of *Ligustrum lucidum* have been used as an antipyretic, analgesic, and anti-inflammatory agent. The leaves of *Ligustrum japonicum* have also been used to treat illnesses such as ophthalmalgia, ulcerative stomatitis, mastitis, swelling, and burn. The fruits of *Ligustrum lucidum* taste bitter and are nontoxic. Treatment dosage of the dried fruits is typically 6 to 20 g per day. That of the dried leaves is typically 40 to 75 g per day.

A Chinese herbal medicine known as LONICERAE FLOS has traditionally been used to treat illnesses such as fever, acute infectious diseases, measles, carbuncle, dysentery, enteritis, ringworm and similar skin diseases. LONICERAE FLOS is prepared from the dried flower bud of *Lonicera japonica* or *Lonicera confusa*. Both plants belong to the family Caprifoliaceae. The flower of *Lonicera japonica* has diuretic, antipyretic, anti-inflammatory, anti-convulsive, antibacterial and antiviral properties. The flower bud has also been used as a diuretic. The herbal medicine tastes sweet and is nontoxic. Treatment dosage is typically 11 to 75 g per day for the typical human.

Ho et al. disclose the anti-HIV activity in vitro of a mixture of *Lonicera japonica, Isatis tinctoria* (or *Isatis indigotica*) and *Polygonum bistorta* or a mixture of *Lonicera japonica* with *Scutellaria baicalensis*. Water extractions of the mixtures, treatment with ethanol precipitation and charcol adsorption are disclosed for the preparation of the anti-HIV active composition. See D. D. Ho & X. S. Li, U.S. Pat. No. 5,178,865, issued on Jan. 12, 1993. Several tannins such as caffeoylquinates isolated from *Lonicera japonica* have been reported to have an inhibitory effect on HIV-1 reverse transcriptase activity. See C.-W. Chang, M.-T. Lin, S.-S. Lee, K. C. S. C. Liu, F.-L. Hsu, & J.-Y. Lin, *Antiviral Research*, 27, 367–374 (1995).

A mixture of aqueous extracts of *Lonicera japonica* flower buds and *Forsythia suspensa* fruits with the crude flavonoids from *Scutellaria baicalensis* has been shown to have antibacterial and antiviral properties. A group of patients with severe respiratory disease were treated with the mixture and they responded as well as a control group on standard antibiotic therapy. See P. J. Houghton, Z. Boxu, & Z. Xisheng, *Phytother. Res.*, 7, 384–386 (1993).

A Chinese herbal medicine known as PHELLODENDRI CORTEX has traditionally been used to treat illnesses such as dysentery, diarrhea, jaundice, stools with blood, abdominal pain, indigestion, bacteroid enteritis, and tuberculoid diarrhea. The herbal medicine has also been used to prepare an eye wash, for strengthening stomach and intestine to stimulate appetite, and as an astringent, anti-inflammatory, etc. It has antibacterial, anti-inflammatory, and wound healing properties. PHELLODENDRI CORTEX is prepared from the dried cortex of plants from the Rutaceae family such as *Phellodendron amurense, Phellodendron chinense, Phellodendron amurense var. sachalinense*, and *Phellodendron wilsonii*. PHELLODENDRI CORTEX tastes bitter and is nontoxic. Treatment dose is typically 1 to 11 g per day.

Hozumi et al. disclose the bark of *Phellodendron amurense* as antiherpesviral, antipolioviral, anti-measles virus, anti-varicella-zoster virus, and anti-CMV agents, as well as an anti-DNA virus and anti-RNA virus agent. See T. Hozumi, T. Matsumoto, H. Ooyama, T. Namba, K. Shiraki, M. Hattori, M. Kurokawa, & S. Kadota, U.S. Pat. No. 5,411,733, issued on May 2, 1995.

A Chinese herbal medicine known as POLYGONI CUSPIDATI RHIZOMA has traditionally been used to treat illnesses such as dysentery, menorrhagia, dysmenorrhea, dysuria, infantile growth retardation, and appendicitis. POLYGONI CUSPIDATI RHIZOMA is prepared from the dried rhizoma of *Polygonum cuspidatum, Polygonum runcinatum*, or *Polygonum reynoutria* (also known as *Reynoutria japonica*) which belong to the family Polygonaceae. The tender leaf has also been used to treat contusion and cut injuries. Extract of the herbal medicine has exhibited antibacterial and antiviral effects in vitro. Excessive use of the herbal medicine may cause a slight diarrhea. The herbal medicine tastes bitter and the treatment dose is typically 6 to 40 g per day.

Hozumi et al. disclose the root and rhizome of *Polygonum cuspidatum* as an antiherpesviral, antipolioviral, anti-varicella-zoster virus, and anti-CMV agent. See T. Hozumi, T. Matsumoto, H. Ooyama, T. Namba, K. Shiraki, M. Hattori, M. Kurokawa, & S. Kadota, U.S. Pat. No. 5,411,733, issued on May 2, 1995.

Resveratrol has been reported as an antifungal and antibacterial component in the root of *Polygonum cuspidatum*. See H. Y. Hsu, Y. P. Chen, & M. Hong, *The Chemical Constituents Of Oriental Herbs*, Vol. 2, Oriental Healing Arts Institute, Los Angeles, Calif., U.S.A., 51 (1985).

A Chinese herbal medicine known as PRUNELLAE SPICA has traditionally been used to treat illnesses such as goiter, hemorrhoids, swollen eye, ophthalmalgia, gonorrhea, uterine disease, mastitis, breast abscess, breast cancer, chronic arthritis, conjunctivitis, and hypertension. PRUNELLAE SPICA is prepared from the dried spica or whole plant of *Prunella vulgaris* or *Prunella vulgaris subsp. asiatica* (also known as *Prunella vulgaris var. lilachina*). Both plants belong to the family Labiatae. The whole plant can be used as a diuretic and also has antibacterial effect in vitro. The herbal medicine tastes bitter and is nontoxic. Treatment dosage is typically 4 to 110 g per day for the average human.

Hozumi et al. disclose the spike of *Prunella vulgaris* as an antiherpesviral agent for treating herpes virus infection. See T. Hozumi, T. Matsumoto, H. Ooyama, T. Namba, K. Shiraki, M. Hattori, M. Kurokawa, & S. Kadota, U.S. Pat. No. 5,411,733, issued May 2, 1995. The water extract of *Prunella vulgaris* (boiling 3 g in 100 mL water for 45 minutes) has also been reported to have anti-HIV (strain H9/3B) activity. The extract also exhibited synergistic anti-HIV activity with zidovudine (AZT) and didanosine (ddI). Only a slight additive effect was observed for *Prunella vulgaris* and zalcitabine (ddC). See J. F. John, R. Kuk, & A. Rosenthal, *Abstr. Gen. Meet. Am. Soc. Microbiol.*, 94, 481 (1994).

Yamasaki et al. evaluate in vitro two hundred four (204) crude drugs of common use in Japan for anti-HIV-1 activity and reported that the hot water extract of *Prunella vulgaris* (spike) showed a strong in vitro anti-HIV-1 activity with an $IC_{100}$ of 16 µg/mL. See K. Yamasaki, T. Otake, H. Mori, M. Morimoto, N. Ueba, Y. Kurokawa, K. Shiota, & T. Yuge, *Yakugaku Zasshi*, 113(11), 818–824 (1993).

Yao et al. reported that the water extract of the dried entire plant of *Prunella vulgaris* was active in vitro in inhibiting HIV-1 replication with relatively low cytotoxicity towards the MT-4 cells. The extract was also active in reverse transcriptase inhibition. The active factor was purified and identified as anionic with a molecular weight of approximately 10,000 dalton. This active component may be the same as the prunellin, as described below by Tabba, et al. The purified extract inhibited HIV-1 replication in the lymphoid cell line MT-4, in the monocytoid cell line U937, and in peripheral blood mononuclear cells (PBMC) at effective concentrations of 6, 30, and 12.5 µg/mL, respectively. Pretreatment of uninfected cells with the extract prior to viral exposure did not prevent HIV-1 infection. Preincubation of HIV-1 with the purified extract dramatically decreased infectiousness. The purified extract was also able to block cell-to-cell transmission of HIV-1, prevented syncytium formation, and interfered with the ability of both HIV-1 and purified gp120 to bind to CD4. PCR (polymerase chain reaction) analysis confirmed the absence of HIV-1 proviral DNA in cells exposed to virus in the presence of the extract. The results suggested that the purified extract antagonized HIV-1 infection of susceptible cells by preventing viral attachment to the CD4 receptor. See X. J. Yao, M. A. Wainberg, & M. A. Parniak, *Virology*, 187(1), 56–62 (1992).

Tabba et al. isolated and partially characterized an anti-HIV component, prunellin, from aqueous extracts of dried inflorescence of *Prunella vulgaris*. Prunellin is a carbohydrate with an MIC (minimum inhibition concentration) of 2.2 μg/mL against HIV-1 in vitro. It was identified as a partially sulfated polysaccharide with a molecular weight of about 10,000 dalton. See H. D. Tabba, R. S. Chang, & K. M. Smith, *Antiviral Research*, 11, 263–273 (1989).

Zheng evaluated four hundred seventy two (472) traditional medicinal herbs for antiviral effect on type 1 herpes simplex virus (HSV 1). *Prunella vulgaris* was one of the ten herbs found to be highly effective in vitro. Clinically, 78 cases of herpetic keratitis due to HSV1 were treated with *Prunella vulgaris* and *Pyrrosia lingua* eye drops. Among them, 38 cases were effectively cured, 37 cases showed an improvement, and 3 cases showed no benefit. See M. Zheng, *J. Tradit. Chin. Med.*, 8(3), 203–206 (1988).

Triterpene 1 and triterpene 2 which have been isolated from *Prunella vulgaris* have shown antiviral activity against HSV1. Triterpene 1 was identified as betulinic acid and triterpene 2 was identified as 2α, 3α-dihydroxyurs-12-en-28-oic acid. The $EC_{50}$ was estimated to be 30 μg/mL for triterpene 1 and 8 μg/mL for triterpene 2 by plaque reduction assay. See S. Y. Ryu, C-K. Lee, C. O. Lee, H. S. Kim, & O. P. Zee, *Arch. Pharmacal Res.* (Seoul), 15(3), 242–245 (1992).

A Chinese herbal medicine known as SCUTELLARIAE BARBATAE HERBA has traditionally been used to treat illnesses such as hematemesis, gonorrhea with traces of blood, sores, cancer, convulsion, pneumonia, enteritis, coccygodynia, appendicitis, asthma, malaria, and rheumatism. It was also found to have antibacterial effect. SCUTELLARIAE BARBATAE HERBA is prepared from the dried whole plant of *Scutellaria barbata, Scutellaria rivularis*, or *Scutellaria dependens* which belong to the family Labiatae. The herbal medicine tastes bitter and should not be consumed by those who have anemia. Pregnant women should avoid taking this herb. Treatment dosage is typically 4 to 300 g per day.

Dried whole plants of *Scutellaria rivularis* have been used in folk medicine for the treatment of tumors, hepatitis, liver cirrhosis, and other diseases in China and Taiwan. See Y. L. Lin, Y. H. Kuo, G. H. Lee, and S. M. Peng, *J. Chem. Research* (S), 320–321 (1987).

Apigenin, isolated from the whole herb of *Scutellaria rivularis*, was found to have anti-influenza virus activity. See T. Nagai, et al., *Chem. Pharm. Bull.*, 38(5), 1329–1332 (1990).

A Chinese herbal medicine known as SOLANI HERBA has traditionally been used to treat illnesses such as boil, acute nephritis, cancer and sores. SOLANI HERBA is prepared from the dried whole plant of *Solanum nigrum* which belongs to the family Solanaceae. The extract of SOLANI HERBA has demonstrated anti-inflammatory property. The fruit has also exhibited the effects of suppressing coughs and relieving bronchial inflammation. The herbal medicine tastes bitter and slightly sweet, and is nontoxic. Treatment dosage is typically 11 to 60 g per day.

The compound solasonine (found in the whole herb, fruit, leaf, and fresh immature berries of *Solanum nigrum*) has an anti-inflammatory effect similar to cortisone. Solasonine and solanine (also found in *Solanum nigrum*) possess the ability of raising or lowering the blood sugar level in rats depending on the situation of the animals. Solasonine was also reported to have a stimulating effect on the heart, while solanine had a suppressive effect. When administered at small doses, solasonine enhances the stimulative process of the central nerve system in animals (i.e., rat and rabbit). On the other hand, it enhances the suppressive process when administered at large doses. Solasonine can also lower the blood coagulability. See (1) H. Y. Hsu, Y. P. Chen, S. G. Hsu, J. S. Hsu, C. J. Chen, & H. C. Chang, *Concise Pharmacognosy*, New Medicine Publishing Co., Taipei, R.O.C., 176–177 (1985); (2) H. Y. Hsu, Y. P. Chen, & M. Hong, *The Chemical Constituents Of Oriental Herbs*, Oriental Healing Arts Institute, Los Angeles, Calif., U.S.A., 1400–1401, 1406 (1982); and (3) H. Y. Hsu, Y. P. Chen, & M. Hong, *The Chemical Constituents Of Oriental Herbs*, Vol. 2, Oriental Healing Arts Institute, Los Angeles, Calif., U.S.A., 742 (1985).

Combinations of herbal medicines such as LONICERAE FLOS, BAPHICACANTHIS RHIZOMA ET RADIX, and FORSYTHIAE FRUCTUS have been used as antipyretic and detoxification agents and for treating acute hepatitis. The herbal medicines BLECHNI RHIZOMA and POLYGONI CUSPIDATI RHIZOMA have been used along with other herbal medicines in a formula for treating Hepatitis B. The herbal medicines SCUTELLARIAE BARBATAE HERBA and LIGUSTRI FRUCTUS have occasionally been added with other herbal medicines into the above formula to improve the treatment. The herbal medicine LIGUSTRI FRUCTUS was occasionally used along with other herbal medicines mainly as a tonic and the herbal medicine HEDYOTIS has been occasionally used along with other herbal medicines as a detoxification agent. The herbal medicine PRUNELLAE SPICA has also been used along with other herbal medicines to relief liver stress.

Chang and Yeung screened the boiling water extracts of twenty seven (27) medicinal herbs for anti-HIV activity. They found eleven (11) of the extracts were active in inhibiting HIV in the H9 cells. Lonicera japonica, *Prunella vulgaris, Woodwardia unigemmata*, and *Senecio scandens* were among those active ones with moderate activities. *Forsythia suspensa, Isatis tinctoria*, and *Polygonum cuspidatum* were among those tested which did not display activity in the anti-HIV assay. The anti-HIV active extract of *Viola yedoensis* was further tested and found to be fairly specific. The extract did not inactivate HIV extracellularly and did not inhibit the growth of herpes simplex, polio, or vesicular stomatitis viruses in human fibroblast culture. See R. S. Chang & H. W. Yeung, *Antiviral Research*, 9, 163–175 (1988).

Antiviral agents have been isolated from *Syzygium aromaticum, Sapium sebiferum, Scutellaria baicalensis*, and *Scutellaria rivularis*. Eugeniin (a tannin) isolated from *Syzygium aromaticum* and methyl gallate isolated from *Sapium sebiferum* exhibited anti-herpes simplex virus activity in vitro. Plant flavenoids, such as 5,7,4'-trihydroxy-8-methoxyflavone from the root of *Scutellaria baicalensis* and apigenin (5,7,4'-trihydroxyflavone) from the whole herb *Scutellaria rivularis*, were also reported to have anti-influenza virus activity. See (1) T. Hozumi, et al., U.S. Pat. No. 5,411,733 (1995); (2) M. Takechi & Y. Tanaka, *Planta Medica*, 42, 69–74 (1981); (3) C. J. M. Kane, et al, *Bioscience Reports*, 8, 85–94 (1988); and (4) T. Nagai, et al., *Chem. Pharm. Bull.*, 38(5), 1329–1332 (1990).

Hozumi et al. investigated ninety one (91) herbal medicines which demonstrated antiviral activity. More specifically, fifty two (52) of them had antiherpesviral activity, sixty four (64) had antipolioviral activity, thirty seven (37) had anti-measles virus activity, twenty seven (27) had anti-varicella-zoster virus activity, twenty three (23) had anti-CMV activity, and twenty eight (28) had anti-DNA virus and anti-RNA virus activity. See T. Hozumi, T. Matsumoto, H. Ooyama, T. Namba, K. Shiraki, M. Hattori, M. Kurokawa, & S. Kadota, U.S. Pat. No. 5,411,733, issued on May 2, 1995. The anti-DNA virus and anti-RNA virus activity of the twenty eight (28) herbal medicines disclosed in the 5,411,733 patent was based upon their antiherpesviral, antipolioviral, anti-measles virus, and/or anti-varicella-zoster virus and anti-CMV activities. However, the extrapolation to cover both anti-DNA virus and anti-RNA virus activities is unfounded from the experiments conducted.

The data of the present invention, presented below, evidenced little or no anti-HIV activity of the two herbal medicines at 2.5 and 0.5 mg/mL derived from the rhizome of *Cyrtomium fortunei* and the bark of *Phellodendron amurense*. In contrast, the three (3) herbal medicines using the spike of *Prunella vulgaris*, the fruit of *Forsythia suspensa*, and the root and rhizome of *Polygonum cuspidatum* will be shown to have a strong to moderate anti-HIV activity at 2.5 mg/mL. *Prunella vulgaris* has also been reported by others as described above to have a very good anti-HIV activity.

It is noted that in the practice of traditional Chinese medicine, herbal medicines are used to treat the symptoms of the patients, not the disease or causative agent itself, and are therefore not known to be specific to a particular disease. Herbal medicines were prescribed depending on the symptoms of the individual patient. The composition of herbal medicines also vary case by case and may even change for each individual patient during the course of the treatment according to each treatment result. It is therefore very difficult to describe a particular herbal composition from the prior art suitable for treating a specific disease.

The present invention is directed to the discovery of antiviral herb compositions, extracts thereof and the active chemical constituents thereof. The antiviral herb compositions of this invention are derived from individual herbs, herb mixtures and commercially available Chinese herbal medicines. These novel herb compositions and their extracts and/or active principles are demonstrated herein as active against viral diseases such as HBV and HCV carriers, hepatitis B, hepatitis C, HIV infection and AIDS.

SUMMARY OF THE INVENTION

As used herein and in the claims, the following nomenclatures will be used to identify the four (4) herb mixtures known as HHT888-4, HHT888-5, HHT888-45 and HHT888-54.

HHT888-4 is a mixture of five (5) single-herb Chinese herbal medicines at a preferred ratio of No.4(1):No.4(2):No.4(3):No.4(4):No.4(5) of about 3:3:3:3:4 (w/w). The weight ratio may vary up to 50% per component. By "variance of the weight ratio by 50%" means that each value of each component of the ratio may be increased or decreased by 50%. Thus, as an example, 1:1 can range from 1.5:0.5 to 0.5:1.5 (or 3:1 to 1:3).

HHT888-5 is a mixture of eleven (11) single-herb Chinese herbal medicines, No.5(1) to No.5(11), preferably at about equal proportions by weight. The weight ratio may vary up to 50% per component.

HHT888-45 is a mixture of four (4) to six (6) single-herb Chinese herbal medicines at a preferred ratio of No.4(3): No.4(4): No.5(4): No.5(5): No.5(8): No.4(2) of about 1:1:1:1:0–1:0–1 (w/w). The weight ratio may vary up to 50% for each component.

HHT888-54 is a mixture of No.5(5) or H and at least one single-herb medicine selected from No.4(2), No.4(3), No.4(4), No.4(5), No.5(1), No.5(2), No.5(4), No.5(7), No.5(8) and No.5(11), wherein the preferred weight ratio of No.5(5) or H to each of the other single-herb medicines is 1:1. Thus, HHT888-54, in a preferred embodiment, consists of No.5(5) or H plus No.4(3), No.4(4), No.5(8) and No.5(11); the preferred weight ratio is 1:1:1:1:1. More generally, the weight ratio of No.5(5) or H to the sum of the other single-herb medicines is from 1:10 to 10:1.

The single-herb components of HHT888-4 are:
No.4(1)=HEDYOTIS (also known as OLDENLANDIAE HERBA) source: *Hedyotis diffusa* (also known as *Oldenlandia diffusa*)
No.4(2)=SCUTELLARIAE BARBATAE HERBA source: *Scutellaria barbata, Scutellaria rivularis, Scutellaria dependens*
No.4(3)=LONICERAE FLOS source: *Lonicera japonica, Lonicera confusa*
No.4(4)=PRUNELLAE SPICA source: *Prunella vulgaris, Prunella vulgaris subsp. asiatica* (also known as *Prunella vulgaris var. lilachina*)
No.4(5)=SOLANI HERBA source: *Solanum nigrum*

The single-herb components of HHT888-5 are:
No.5(1)=HEDYOTIS (also known as OLDENLANDIAE HERBA) source: *Hedyotis diffusa* (also known as *Oldenlandia diffusa*)
No.5(2)=BLECHNI RHIZOMA or DRYOPTERIS CRASSIRHIZOMAE RHIZOMA source: *Blechnum orientale, Dryopteris crassirhizoma, Osmunda japonica, Woodwardia orientalis, Woodwardia unigemmata, Athyrium acrostichoides, Sphaeropteris lepifera, Cyrtomium falcatum, Cyrtomium fortunei*
No.5(3)=CIRSII RHIZOMA ET RADIX and BREEAE RADIX source: *Cirsium japonicum, Cirsium albescens, Cirsium japonicum var. australe, Breea segetum* (also known as *Cephalanoplos segetum*), *Breea setosum*
No.5(4)=LESPEDEZAE HERBA or SENECINIS HERBA source: *Lespedeza cuneata, Senecio scandens*
No.5(5)=AEGINETIAE HERBA (a.k.a GOLDEN LOCK KEY or LOTUS HERBA). source: *Aeginetia indica Dichondra micrantha, Striga lutea Dichondra repens.*
No.5(6)=BAPHICACANTHIS RHIZOMA ET RADIX source: *Baphicacanthes cusia, Strobilanthes cusia, Isatis tinctoria, Isatis indigotica, Polygonum tinctorium*
No.5(7)=POLYGONI CUSPIDATI RHIZOMA source: *Polygonum cuspidatum, Polygonum runcinatum, Polygonum reynoutria* (also known as *Reynoutria japonica*)
No.5(8)=FORSYTHIAE FRUCTUS source: *Forsythia suspensa, Forsythia viridissima, Forsythia koreana*
No.5(9)=PHELLODENDRI CORTEX source: *Phellodendron amurense, Phellodendron chinense, Phellodendron amurense var. sachalinense, Phellodendron wilsonii*
No.5(10)=BLETILLAE TUBER source: *Bletilla striata*
No.5(11)=LIGUSTRI FRUCTUS source: *Ligustrum lucidum, Ligustrum japonicum*

The single-herb components of HHT888-45 are:
No.4(3)=LONICERAE FLOS source: *Lonicera japonica, Lonicera confusa*
No.4(4)=PRUNELLAE SPICA source: *Prunella vulgaris, Prunella vulgaris subsp. asiatica* (also known as *Prunella vulgaris var. lilachina*)
No.5(4)=LESPEDEZAE HERBA or SENECINIS HERBA source: *Lespedeza cuneata, Senecio scandens*

No.5(5)=AEGINETIAE HERBA source: *Aeginetia indica Dichondra micrantha, Striga lutea, Dichondra repens.*

No.4(2)=SCUTELLARIAE BARBATAE HERBA (optional) source: *Scutellaria barbata, Scutellaria rivularis, Scutellaria dependens*

No.5(8)=FORSYTHIAE FRUCTUS (optional) source: *Forsythia suspensa, Forsythia viridissima, Forsythia koreana*

The single-herb components of HHT888-54 are: in addition to No. 5(5) are at least one selected from:

No.5(5)=AEGINETIAE HERBA (a.k.a. GOLDEN LOCK KEY or LOTUS HERBA). source: *Aeginetia indica*; or H=DICHONDRAE HERBA source: *Dichondra repens* or *Dichondra micrantha*; and at least one selected from:

No.4(2)=SCUTELLARIAE BARBATAE HERBA source: *Scutellaria barbata, Scutellaria rivularis, Scutellaria dependens*

No.4(3)=LONICERAE FLOS source: *Lonicera japonica, Lonicera confusa*

No.4(4)=PRUNELLAE SPICA source: *Prunella vulgaris, Prunella vulgaris subsp. asiatica* (also known as *Prunella vulgaris var. lilachina*)

No.4(5)=SOLANI HERBA source: *Solanum nigrum*

No.5(1)=HEDYOTIS (also known as OLDENLANDIAE HERBA) source: *Hedyotis diffusa* (also known as *Oldenlandia diffusa*)

No.5(2)=BLECHNI RHIZOMA or DRYOPTERIS CRASSIRHIZOMAE RHIZOMA source: *Blechnum orientale, Dryopteris crassirhizoma, Osmunda japonica, Woodwardia orientalis, Woodwardia unigemmata, Athyrium acrostichoides, Sphaeropteris lepifera, Cyrtomium falcatum, Cyrtomium fortunei*

No.5(4)=LESPEDEZAE HERBA or SENECINIS HERBA source: *Lespedeza cuneata, Senecio scandens*

No.5(7)=POLYGONI CUSPIDATI RHIZOMA source: *Polygonum cuspidatum, Polygonum runcinatum, Polygonum reynoutria* (also known as *Reynoutria japonica*)

No.5(8)=FORSYTHIAE FRUCTUS source: *Forsythia suspensa, Forsythia viridissima, Forsythia koreana*

No.5(11)=LIGUSTRI FRUCTUS source: *Ligustrum lucidum, Ligustrum japonicum*

It should be noted that No.4(1) is the same as No. 5(1) (HEDYOTIS). The names of the Chinese herbal medicines for the single-herb components are shown in capital letters, followed by their plant sources listed in italics.

As used herein and in the claims, the term HHT888-4, HHT888-5, HHT888-45 and HHT888-54 include the actual herbal blends, aqueous extracts thereof and the active components or principles of the extract. In similar fashion, the use of the terms No.5(5), No.5(8) and the like include the actual herb, extracts thereof and the isolated active molecular agents.

As also used in the specification and in the claims, G is the herb *Aeginetia indica* or a source plant of No.5(5). No.4(2), No.4(3), No.4(4), No.4(5), No. 5(1), No.5(2), No.5(3), No.5 (4), No.5(5), No.5(6), No.5(7), No.5(8), No.5(9), No. 5(10), No.5(11) and H are the single-herb components described above, including their respective source plants.

Specific descriptions of the above recited Chinese herbal medicines and medicinal herbs can be found in the following references: (1) H. C. Chang, *Medicinal Herbs I*, Holiday Publishing Co., Taipei, Taiwan, R.O.C., 15, 36, 100, 113, 127, 147 (1990); (2) H. C. Chang, *Medicinal Herbs II*, Holiday Publishing Co., Taipei, Taiwan, R.O.C., 15, 27, 131, 135, 155 (1991); (3) W. S. Kan, *Pharmaceutical Botany*, National Research Institute Of Chinese Medicine, Taipei, Taiwan, R.O.C., 113, 124–130, 200–201, 206–207, 289–290, 353–354, 442–444, 460–461, 485, 487–488, 497, 505, 513–514, 522, 527–529, 558, 562–563, 648–649 (1971); (4) M. S. Lee, *Frequently Used Chinese Crude Drugs And Folk Medicines Handbook*, 12th Ed., Sheng-Chang Medicinal Record Magazine Publishing Co., Taipei, Taiwan, R.O.C., 4–6, 17, 21, 29, 36, 38, 40, 48, 58, 64, 71, 79, 85 (1992); and (5) H. Y. Hsu, Y. P. Chen, S. G. Hsu, J. S. Hsu, C. J. Chen, & H. C. Chang, *Concise Pharmacognosy*, New Medicine Publishing Co., Taipei, Taiwan, R.O.C., 90, 97, 105–106, 117–118, 126–127, 130–131, 133, 138, 144–145, 152–153, 156–157, 161–162, 174, 176–177, 357–358, 381–382, 384–385, 456–457, 577–578 (1985).

The present invention in its broadest aspect relates to the described herbal medicine mixtures and their use to prevent and treat viral infections. The invention also relates to novel combinations of medicinal herbs and the herbal medicines derived therefrom. For example, the herbal mixtures designated HHT888-4, HHT888-5, HHT888-45, HHT888-54, No.5(5)-H, No.5(5)-No.4(3), No.5(5)-No.4(4), No.4(3)-No. 4(4), No.5(5)-No.5(11), H-No.4(4), H-No.4(3), H-No.4(5), H-No.5(8), H-No.5(11), mixtures thereof and their pharmaceutically acceptable salts and the like. More specifically, the viral infections are those caused by HBV, HCV and HIV. The antiviral mixtures according to the invention have been described above as HHT888-4, HHT888-5, HHT888-45 and HHT888-54. In addition, the single herb agents designated No.4(2), No.4(5), No.5(5), No.5(7), No.5(8), No.5(11) and H have been shown to have antiviral activity. These single herb agents have not been shown by the prior art to have antiviral activity.

A more specific aspect of the present invention resides in the discovery that HHT888-5 is efficacious in reducing hepatitis B viruses in HBV carriers. An additional aspect of the invention resides in the discovery that HHT888-45 is efficacious in treating hepatitis C patients and returning their liver function to normal.

The herb mixtures HHT888-4 and HHT888-5 and their aqueous extracts have both been shown by the inventors herein to also have antiretroviral activities against MuLV and HIV in vitro. This evidence strongly supports the conclusion that they have in vivo efficacy. In addition, eleven (11) of the fifteen (15) single-herb components of HHT888-4 and HHT888-5, i.e., No.4(2), No.4(3), No.4(4), No.4(5), No.5(1), No. 5(2), No.5(4), No.5(5), No.5(7), No.5 (8), No.5(11), and the medicinal herb H have shown anti-HIV activities by effectively suppressing viral proliferation in HIV infected human peripheral blood lymphocytes (PBLs). This model is highly predictive of anti-HIV activity in vivo.

The water extract of the single-herb component No.5(5) prepared directly from its source plant, *Aeginetia indica*, has shown good anti-HIV activity. Further, the water extracts of the single-herb components No.4(3), No.4(4), and No.5(11) have shown moderate to strong anti-HIV activities. Water extracts of the single-herb components No.4(2), No.4(5), No.5(1), No.5(4) and No.5(8) have shown only weak anti-HIV activities.

The water extractable and acid precipitable components of No.4(2), No.4(5), No.5(1), No.5(5), No.5(8) and H are shown herein to be active anti-HIV agents. Similar water extractable and acid precipitable components have also been isolated from No.4(4) and No.5(11) and are shown herein to be anti-HIV. These water extractable and acid precipitable anti-HIV active components are similar, have not been described before, and are novel and unobvious.

Water extractable and acid soluble anti-HIV active components have also been isolated from No.4(4) and No.5(11).

The water extractable and acid soluble active component of No.5(11) has not been described before and is novel. The water extractable and acid soluble active component of No.4(4) may be the same as the partially sulfated polysaccharide or prunellin described before. Only one active component has been isolated from the water extract of No.4(3) which is soluble in acid.

There is further disclosed as compositions of matter, the herb mixtures HHT888-4, HHT888-5, HHT888-45 and HHT888-54. These compositions of matter have not been described before and are unobvious.

Further disclosed is a composition of matter comprising at least one of the individual water extractable and acid precipitable anti-HIV active components isolated separately or in combination from the single-herb herbal medicines or their source plants selected from the group consisting of: No.4(2), No.4(4), No.4(5), No.5(1), No.5(5), No.5(8), No.5(11) and H. These compositions of matter have not been described before and are unobvious and novel.

The utility of the present compositions of matter resides in their use in treating viral infections. Thus, there is further disclosed a method of treating viral infections in a mammal, said method comprising administering to said mammal a therapeutically effective amount (such as from 0.4 to 120 g per day) of at least one composition selected from the group consisting of HHT888-4, HHT888-5, HHT888-45, HHT888-54, No.4(2), No. 4(5), No.5(1), No.5(2), No.5(4), No.5(5), No.5(7), No.5(8), No.5(11) and H and their respective extracts or active principles.

More specifically, there is disclosed a method for reducing the viral load of humans infected with HBV, said method comprising administering to said human a therapeutically effective amount (such as from 0.4 to 120 g per day) of a composition comprising HHT888-5 or an extract obtained from HHT888-5.

There is also disclosed a method for treating humans infected with HCV, said method comprising administering to said human a therapeutically effective amount (such as from 0.4 to 120 g per day) of a composition comprising HHT888-45 or an extract obtained from HHT888-45.

There is also disclosed a method of reducing the viral load of a human carrier of the HBV and a method of treating or preventing hepatitis B in a human, said method comprising administering to said human a therapeutically effective amount (such as from 0.4 to 120 g per day) of at least one composition selected from No.5(5) and at least one agent selected from the group consisting of No.5(1), No.5(2), No.5(3), No.5(4), No.5(6), No.5(7), No.5(8), No.5(9), No.5(10), and No.5(11).

There is further disclosed a method of treating a HCV carrier and a method of treating or preventing hepatitis C in a human, said method comprising administering to said human a therapeutically effective amount (such as from 0.4 to 120 g per day) of a composition comprising the mixture of the single-herb herbal medicine No.5(5), its extract or active principle and at least one single-herb herbal medicine, its extract or active principle selected from the group consisting of No.4(2), No.4(3), No.4(4), No.5(4), No.5(8), and No.5(11).

Also disclosed is a method of treating hepatitis B in a human, said method comprising administering to said human a therapeutically effective amount (such as 0.4 to 120 g per day) of at least one composition selected from HHT888-45 and HHT888-5.

There is further disclosed a method of treating hepatitis B in a human, said method comprising administering to said human a therapeutically effective amount (such as from 0.4 to 120 g per day) of at least one composition selected from: (1) a mixture of the single-herb herbal medicine No.5(5), its extract or active principle and at least one single-herb herbal medicine, its extract or active principle selected from the group consisting of No.4(2), No.4(3), No.4(4), No.5(4), No.5(8), and No.5(11); and (2) a mixture of the single-herb herbal medicine No.5(5), its extract or active principle and at least one single-herb herbal medicine, its extract or active principle selected from the group consisting of No.5(1), No.5(2), No.5(3), No.5(4), No.5(6), No.5(7), No.5(8), No.5(9), No.5(10), and No.5(11).

There is further disclosed a method for treating humans infected with HIV, said method comprising administering to said human a therapeutically effective amount (such as 0.4 to 120 g per day) of a composition comprising HHT888-4.

There is disclosed a method for treating humans infected with HIV, said method comprising administering to said human a therapeutically effective amount (such as 0.4 to 120 g per day) of a composition comprising HHT888-5.

There is disclosed a method for treating humans infected with HIV, said method comprising administering to said human a therapeutically effective amount (such as 0.4 to 120 g per day) of a composition comprising HHT888-45.

There is disclosed a method for treating humans infected with HIV, HBV and HCV, said method comprising administering to said human a therapeutically effective amount (such as 0.4 to 120 g per day) of a composition comprising HHT888-54.

There is also disclosed a method for treating humans infected with HIV, said method comprising administering to said human a therapeutically effective amount of a composition comprising at least one single-herb herbal medicine, its extract or active principle selected from the group consisting of No.4(2), No.4(5), No.5(1), No.5(2), No.5(4), No.5(5), No.5(7), No.5(8), No.5(11) and H.

There is also disclosed novel herbal blends and a method of treating humans infected with HIV, said method comprising administering to said human a therapeutically effective amount of an herbal blend comprising at least one herbal medicine selected from No.5(5) H and and mixtures thereof, and at least one herbal medicine selected from the group consisting of No.4(2), No.4(3), No.4(4), No.4(5), No.5(1), No.5(2), No.5(4), No.5(7), No.5(8) and No.5(11).

Also disclosed is a method for treating humans infected with HIV, said method comprising administering to said human a therapeutically effective amount of a mixture comprising at least two antiviral components isolated from the single-herb herbal medicines or their source plants selected from the group consisting of No.4(2), No.4(3), No.4(4), No.4(5), No.5(1), No.5(2), No.5(4), No.5(5), No.5(7), No.5(8), No.5(11), and H.

Also disclosed is a method for treating humans infected with HIV, said method comprising administering to said human a therapeutically effective amount of a composition comprising at least one of the water extractable and acid precipitable antiviral components or compounds isolated from the single-herb herbal medicines or their source plants selected from the group consisting of No.4(2), No.4(4), No.4(5), No.5(1), No.5(5), No.5(8), No.5(11) and H.

Thus, the present invention is directed to: 1) compositions of matter (i.e., herbal blends and isolated chemical entities); 2) methods for the treatment of HBV and HCV carriers; 3) prevention and treatment of hepatitis B and hepatitis C; 4) treatment of HIV carriers; and 5) prevention and treatment of AIDS through the administration of the compositions according to the present invention.

The dosage of the compositions of the invention can range from 0.4 to 120 g per day for the mammal in need of therapy.

One skilled in the art will appreciate that depending upon the weight of the individual and the progression of the viral infection, that higher doses of the compositions may be required. As the compositions according to the invention have demonstrated virtually no side effects, high doses may be initiated with reduction of dosage upon manifestation (i.e., reduction of viral load) of therapeutic effect. One skilled in the art can tailor each dosage rate for a given individual without undue experimentation. More specifically, the dosages for a given composition can range from 0.4 to 100 g per day, more preferably 1.0 to 25 g per day. Preferably, the compositions are administered at least three (3) times per day, however, bolus administration will be effective. More specifically, an oral dosage of 5.5 g three (3) times a day (total 16.5 g per day) of HHT888-5 has been found to be effective to reduce HBV load in carriers. Oral dosage of 2.7–5.7 g three (3) times a day (total 8–17 g per day) of the herb mixture HHT888-45 has been found to be effective to return normal liver function to hepatitis C patients. Dosages as high as 121 g per day for HHT888-5 and 63 g per day for HHT888-45 have not evidenced serious side effects. It should be appreciated that the dosages recited herein are for the herbal medicine (extract deposited on ground plant or adsorbent) in dry form. Further, extracts of the inventive compositions will increase the concentration of the actives and therefore reductions in the dosage levels will be realized. Dosages as low as 10% of those recited herein for the inventive compositions are contemplated. The preferred dosage for No.5(5) to treat HCV infection is from 0.4 to 17 g per day.

The compositions of the invention are preferably administered orally or enterally, however, intravenous (i.v.) and/or intramuscular (i.m.) administration is also contemplated herein. Those skilled in the art will understand how i.v. and i.m. formulations can be prepared and how the effective dosages can be obtained.

In the method according to this invention a mammal may be a human or animal. The human may be an adult, child or infant. Thus, for infants, an infant formula containing the hereinafter described plant extracts or active principles will be effective in treating the infants infected with HBV, HCV, or HIV. For children and adults, a medical food or nutritional product, such as milks and yogurts, containing the plant extracts or active principles described herein will also be effective in treating humans infected with HBV, HCV, or HIV.

The present invention also relates to a process to isolate the efficacious compounds from the recited herbal medicines or medicinal plants and to the isolated compounds themselves.

The herbs used as starting materials for this invention may be obtained from commercial sources as single-herb herbal medicines which may be mixed, or extracted and concentrated, and placed in compositions for the administration to a human. The plant extracts, once isolated from the plant material, may be concentrated and then placed in form suitable for the administration to a human (i.e., pills, capsules and tablets). The active principles, once isolated from the plant or synthesized, may then be placed in compositions for the administration to a human and may take a variety of forms such as capsules, tablets, powder, candies, gels, beverages, teas, nutritional products, and the like.

Also disclosed is a medicinal product produced by the process comprising the steps of: (a) contacting comminuted plant material such as No.5(1) to No.5(11), No.4(2) to No.4(5), H, and mixtures thereof, with water to form an aqueous dispersion; (b) heating the aqueous dispersion to about 100° C. and holding at that temperature for about 0.5 to about 3 hours; (c) separating the insoluble plant material from the aqueous phase; and (d) concentrating the solute contained in the aqueous phase. The concentrated solute may be obtained through freeze drying, spray drying, evaporation or ultrafiltration.

Also disclosed is a medicinal product produced by the process comprising the steps of: (a) contacting comminuted plant material selected from the group consisting of No.4(2), No.4(4), No.4(5), No.5(1), No.5(5), No.5(8), No.5(11), H, and mixtures thereof, with water to form an aqueous dispersion; (b) heating the aqueous dispersion to about 100° C. and holding at that temperature for about 0.5 to about 3 hours; (c) separating the insoluble plant material from the aqueous phase; (d) acidifying the aqueous solution with acid (such as hydrochloric acid) to a pH of less than about 2; (e) separating the acid precipitate from the supernate; and (f) purifying the acid precipitate by dissolving in a neutral or basic solution (such as 0.1 N ammonium bicarbonate) and precipitating again with acid. Optionally, the acid precipitate may be dissolved in 0.1 N ammonium bicarbonate solution and concentrated. The concentrated solute may be obtained through freeze drying, spray drying, evaporation or ultrafiltration.

Representative of the acids that are useful in acidifying the aqueous extracts include hydrochloric acid, phosphoric acid, glacial acetic acid, sulfuric acid and the like. What is important is that the acid have a pKa sufficient to convert the active components to the acid form. The pH of the extract should be less than 3 and most preferably less than 2 for precipitation to occur.

Also disclosed is a medicinal product produced by a process comprising the steps of: (a) contacting at least one herbal medicine selected from: No.4(2), No.4(4), No.4(5), No.5(1), No.5(5), No.5(8), No.5(11), H, and mixtures thereof, with water to form an aqueous dispersion; (b) stirring the aqueous dispersion at ambient temperature for about 0.5 hours or longer, to about 3 preferably 0.5 hours; (c) separating the insoluble plant material from the aqueous phase; (d) acidifying the aqueous solution with acid to approximately a pH of less than 2 to form a precipitate; (e) separating the acid precipitate from the acid supernate; and (f) purifying the acid precipitate. The precipitate may be purified by repetitively dissolving it in 0.1 N ammonium bicarbonate solution and precipitating it again with acid.

This application sets forth the data available on the present discoveries and fully describes the compositions of matter, their preparations, clinical applications, and analytical tools used to characterize the various active components. These and other aspects of the invention will become apparent to those skilled in the art as a result of the following examples which are intended as illustrative of the invention and not limitative.

BEST MODE FOR CARRYING OUT THE INVENTION

To acquaint persons skilled in the art with the principles of the invention, the following Examples are submitted which are intended to be illustrative and not limitative. All percentages are percentages by weight unless otherwise specified.

EXAMPLE 1

Preparation of Herb Mixtures

In the preparation of the herbal compositions according to the invention, Chinese herbal medicines in single herb format were obtained from commercial sources in powder form. The individual single-herb herbal medicines were mixed in the appropriate proportions to prepare each herb mixture.

The herb mixture for HHT888-4 was prepared by mixing No.4(1), No.4(2), No.4(3), No.4(4), and No.4(5) at a ratio of 3:3:3:3:4 by weight. The herb mixture HHT888-5 was prepared by mixing equal weights of No.5(1), No.5(2), No.5(3), No.5(4), No.5(5), No.5(6), No.5(7), No.5(8), No.5(9), No.5(10), and No.5(11).

The herb mixture HHT888-45 was prepared by mixing four (4) to six (6) single-herb herbal medicines No.4(3), No.4(4), No.5(4), No.5(5), No.5(8), and No.4(2) at a ratio of 1:1:1:1:0-1:0-1 by weight. The single-herb herbal medicine No.5(8) or No.4(2), or both, were not used in some cases in HHT888-45 for initial administrations. One of the two single-herb herbal medicines or both were added later when needed to enhance the therapy. The weight ratio of the single-herb herbal medicine No.4(2) in the herb mixture HHT888-45 also varied case-by-case between 0.5 and 1 when used.

It is noted that a mixture of decoctions prepared individually from the source plants of the single-herb herbal medicines or a decoction prepared from the pre-mixed source plants of the single-herb components of each herb mixture is within the scope of this invention.

EXAMPLE 2

Preparation of Single-herb Herbal Medicines

The plant source from which each single-herb herbal medicine was obtained is listed in the Prior Art and Summary sections of this application. It should be understood that more than one species or genus of medicinal plant may be used to prepare the same herbal medicine. For example, the herbal medicine No.5(8) or FORSYTHIAE FRUCTUS may be prepared from three (3) species of Forsythia genus plants, i.e., *Forsythia suspensa, Forsythia viridissima, Forsythia koreana* or mixtures thereof. The herbal medicine No.5(6) (BAPHICACANTHIS RHIZOMA ET RADIX) may be prepared from one of the five (5) plants *Baphicacanthes cusia, Strobilanthes cusia, Isatis tinctoria, Isatis indigotica, Polygonum tinctorium* or mixtures thereof. The herbal medicines were prepared from their respective plant sources as follows.

A suitable part or parts or the whole plant was obtained, washed with cold water, dried and comminuted. The plant materials were then extracted with boiling water on a basis of 1 part by weight of plant material to approximately 5 to 10 parts by weight of water. The amount of water used should at least cover the plant material in the extraction vessel. Samples were boiled for 0.5 to one hour, but not in excess of 3 hours, in order to allow effective extraction of the desired components. Shorter or longer heating would not substantially affect the extraction, except the yield and cost. The aqueous solution was separated from the plant material by filtration.

The aqueous solution may be freeze dried or spray dried, or reduced in volume by heating with or without an applied vacuum. The concentrate may then be spray dried or freeze dried or absorbed onto a powdered form of the same plant material, starch or other absorbant. Thus the single-herb herbal medicine is prepared.

A decoction is the aqueous solution of the plant material prepared by boiling the plant material in water as described above for about 0.5 to one hour. The decoction may be directly consumed after it is prepared and cooled to warm or ambient temperature or preserved with proper sterilization for later consumption. Sterilization may be accomplished by microfiltration or heat.

EXAMPLE 3

Treatment of Hepatitis B Virus Carriers

Twenty-nine (29) HBV carriers with normal levels of serum glutamine oxalacetate transferase (SGOT) and glutamine pyruvate transferase (SGPT) (liver enzymes), were treated with HHT888-5. Several HBV carriers who had elevated SGOT and SGPT levels were first treated with other remedies which returned their serum liver enzymes to normal levels (8–40 unit/mL for SGOT and 5–35 unit/mL for SGPT) but failed to reduce the HBV load. Treatment with HHT888-5 then began. HHT888-5 was prepared as described in Example 1 by mixing eleven (11) single-herb herbal medicines which were obtained from a commercial source and were manufactured following good manufacture practice (GMP) guidelines. Consent of each patient was obtained before their treatment began.

Patients were instructed to take the HHT888-5 three (3) times a day. Each dose was 5.5 g. Each 5.5 g packet of the herb mixture was mixed with warm water and consumed orally. Serum hepatitis B surface antigen (HBsAg) titers of each patient were determined at intervals as shown in Table 1 to monitor the progress of the treatment. Serum HBsAg titer was determined using a reverse-passive hemagglutination test as described in: (1) *Instruction of "Taifu" Serodia-HBs Test Reagent for HBsAg Detection*, Taifu Pharmaceutical Co., Ltd., Taoyuan, Taiwan, R.O.C.; (2) D. S. Chen & J. L. Sung, *J. Formosan Med Assoc.*, 77, 263–270 (1978); and (3) T. Juji & T. Yokochi, Japan. *J. Exp. Med.*, 39, 615–620 (1969).

Table 1 shows the treatment results of the twenty-nine (29) HBV carriers. Patients showed improvement in their disease state over the course of treatment, as indicated by their HBsAg titer reductions and well being. Fourteen (14) carriers (48%) whose HBsAg titers ranged from 20 to 81,920 were significantly lowered (four to 256-fold reductions, or from positive to negative) after 35 to 964 days of treatment. Four (4) carriers (14%) reduced their HBsAg titers from 20, 40, and 2,560 to negative (i.e., below 20 ng/mL detection level) after 56–153 days of treatment. Fourteen (14) carriers (48%) had no significant change (two-fold titer decrease or increase or no change) in HBsAg titers during the course of the treatment (63–284 days). One carrier (3%) had a slightly four-fold titer increase.

TABLE 1

Clinical Effects of HHT888-5 on Hepatitis B Virus Carriers
HBsAG Titer

| PATIENT | BEFORE | AFTER | DURATION (Days) |
|---|---|---|---|
| 1 | 40 | negative | 56 |
| 2 | 2560 | negative | 72 |
| 3 | 20 | negative | 153 |
| 4 | 20 | negative | 88 |
| 5 | 2560 | 80 | 53 |
| 6 | 1280 | 320 | 101 |
| 7 | 2560 | 1280 | 32 |
|   |   | 1280 | 399 |
|   |   | 320 | 964 |
| 8 | 2560 | 1280 | 79 |
|   |   | 640 | 412 |

TABLE 1-continued

Clinical Effects of HHT888-5 on Hepatitis B Virus Carriers HBsAG Titer

| PATIENT | BEFORE | AFTER | DURATION (Days) |
|---|---|---|---|
| 9 | 20480 | 5120 | 53 |
| 10 | 20480 | 5120 | 60 |
| 11 | 40960 | 10240 | 35 |
| 12 | 81920 | 40960 | 74 |
|  |  | 10240 | 461 |
| 13 | 81920 | 20480 | 63 |
| 14 | 5120 | 2560 | 170 |
|  |  | 2560 | 245 |
|  |  | 1280 | 556 |
|  |  | 1280 | 832 |
| 15 | 160 | 80 | 284 |
| 16 | 320 | 160 | 198 |
| 17 | 640 | 320 | 276 |
| 18 | 1280 | 640 | 120 |
| 19 | 2560 | 1280 | 69 |
| 20 | 5120 | 2560 | 263 |
| 21 | 20480 | 10240 | 77 |
| 22 | 40960 | 40960 | 120 |
|  |  | 20480 | 210 |
| 23 | 160 | 160 | 227 |
| 24 | 320 | 320 | 79 |
| 25 | 640 | 640 | 157 |
| 26 | 1280 | 1280 | 69 |
| 27 | 40960 | 40960 | 137 |
| 28 | 5120 | 10240 | 63 |
| 29 | 160 | 640 | 121 |

The HHT888-5 treatment set forth in this Example compares very favorably with the currently accepted interferon therapy. The response rates for interferon therapy and HHT888-5 treatment to lower the HBsAg titers in patients infected with HBV are comparable, approximately 40% vs. 48%, respectively. The serum HBsAg clearance rates were also comparable for both, 10 to 15% for interferon therapy and approximately 14% for HHT888-5 treatment. Furthermore, the interferon therapy is typically administered intramuscularly or intravenously, with frequent adverse effects. The HHT888-5 treatment was administered orally (like drinking a tea) with no apparent side effects in all patients treated. Oral administration is much more convenient and more economical than intramuscular or intravenous administration. HHT888-5 can thus be safely and conveniently consumed even on a long-term basis to reduce or control HBV proliferation in HBV carriers and hepatitis B patients.

When the HBV viral load in an HBV carrier can be reduced or maintained at a sufficiently low level, the carrier is much less likely to progress to hepatitis, liver cirrhosis, liver cancer, and death. Thus, HHT888-5 can be used to prevent and treat hepatitis B, or even prevent liver cirrhosis or liver cancer caused by HBV infection.

Since HHT888-5 was administered in this Example by mixing the powder in water first and then consumed orally, isolation of the active components of HHT888-5 and its administration to humans would also be efficacious in the treatment of HBV. Dosages of the herb mixture HHT888-5 as high as 120 g per day have been accomplished without serious side effects.

EXAMPLE 4

Antiretroviral Testing of Herb Mixtures and their Water Extracts

In this example, two herb mixtures, HHT888-4 and HHT888-5, were tested for their antiretroviral activities and found to be active against EMuLV and HIV in an in vitro assay. Two in vitro assays, anti-Ecotropic Murine Leukemia Virus (anti-EMuLV) and anti-HIV, were used to test the antiretroviral activities of the inventive compositions.

The anti-EMuLV assay uses a large, enveloped, RNA-containing retrovirus, EMuLV, which belongs to the same virus family as HIV and has many characteristics that are similar to HIV.

1. Anti-Ecotropic Murine Leukemia Virus Assay

The assay contained two parts, a cytotoxicity test and a virus suppression test. See QBI Protocol 39014 Final Report and QBI Protocol 39016 Final Report, Quality Biotech, Camden, N.J., USA, 1992. Each sample was initially tested for its cytotoxicity to the SC-1 indicator cells which were used for titration of infectious EMuLV in a XC plague assay. Cytotoxicity as reported herein is expressed in terms of percent of control proliferation. The higher the percent means the substance being tested is not toxic to the cells. This is very important as compounds that are highly toxic would skew the interpretation of the assay results. For example, high activity in an HIV assay and a high cytotoxicity (low % of control proliferation) could mean that the test compound is inhibiting the growth of the host cells thereby limiting the growth of the virus. Thus, a false positive on anti-viral activity could be interpreted. See QBI protocol C30015, Quality Biotech, Camden, N.J., USA. Each sample was dispersed in a virus resuspension buffer (50 mM Tris, pH 7.8, 10 mM KCL, 0.1 mM EDTA) without the virus. The solution was then subjected to the XC plague assay under the same conditions as those for the determination of EMuLV titer. A sample was considered cytotoxic if the indicator cells for the assay were less than 50% confluent. A noncytotoxic sample concentration was chosen for the virus suppression test.

In the virus suppression test, each sample was incubated with EMuLV (strain AKV623, titer 2.2–4.2×$10^5$ PFU/mL) in a virus resuspension buffer at 23–25 mg/mL (e.g., 100 mg/4.0 mL) for 12–32 minutes. The treated virus suspension was pH adjusted, if necessary, to within 6.8–7.2 and then tested for its titer in the XC plague assay.

An aliquot (1.5 mL) was diluted in the cell culture medium to the endpoint ($10^0$, $10^{-1}$, $10^{-2}$, $10^{-3}$, $10^{-4}$, $10^{-5}$, $10^{-6}$, $10^{-7}$, and $10^{-8}$ dilutions, or as appropriate). Each dilution was vortexed to resuspend any particulates if present and assayed in duplicate for infectious viral particles by the XC plaque assay. A positive control (virus suspension without treatment) and a negative control (cell culture medium, no virus) were also analyzed concurrently to validate the assay.

Anti-EMuLV activity of the sample was expressed in $\log_{10}$ reduction of the EMuLV titer when compared to the positive control. A sample with $\log_{10}$ titer reduction greater than 0.5 is considered to be active.

HHT888-4 and HHT888-5 were initially tested "as is" and exhibited good antiviral activities (1.0 to 1.4 $\log_{10}$ reduction in viral titer) at 25 mg/mL and 12 minutes of incubation with the virus at room temperature. They were then tested again with a longer incubation time (32 minutes) with the virus at the same concentration. Each sample was also tested for its soluble and insoluble fractions in the above virus resuspension buffer to see if any active component was water soluble. The soluble portion was separated from the insoluble one by centrifuge at room temperature and 10,000×g for 10 minutes. The soluble fraction was divided into two aliquots, one 0.45-μm filtered and one unfiltered, and tested to see if residual particulates have any effect on the activity.

Table 2 summarizes the anti-EMuLV activity test results. The results confirmed that both HHT888-4 and HHT888-5 and their soluble and insoluble fractions have anti-EMuLV activities. The samples caused 1.0 to 2.6 $\log_{10}$ reduction in viral titer when they were incubated with the virus at 23–25 mg/mL for 32 minutes. Microfiltration did not significantly affect the activity of either soluble fraction.

TABLE 2

Anti-Ecotropic Murine Leukemia Virus Activity

| Sample | Treatment | Cytotoxicity* 25 | 2.5 | 0.25 mg/mL | Anti-EMuLV Activity $\log_{10}$ Titer Reduction** |
|---|---|---|---|---|---|
| HHT888-4 | "as is" | Yes | No | No | 1.02 (90%)*** |
|  | "as is" | Yes | No | No | 1.04 (91%)**** |
|  | Soluble | — | — | — | 1.74 (98%)**** |
|  | Soluble, filtered | — | — | — | 1.59 (97%)**** |
|  | Insoluble | — | — | — | 2.64 (99.8%)**** |
| HHT888-5 | "as is" | Yes | No | No | 1.35 (96%)*** |
|  | "as is" | Yes | No | No | 2.10 (99.2%)**** |
|  | Soluble | — | — | — | 2.05 (99.1%)**** |
|  | Soluble, filtered | — | — | — | 1.71 (98.1%)**** |
|  | Insoluble | — | — | — | 1.72 (98.1%)**** |

*Sample was considered cytotoxic if the SC-1 indicator cells for the assay were less than 50% confluent.
**As compared to a working virus suspension with a titer of 2.2–4.2 × $10^5$ PFU/mL (plaque forming units/ml), or $\log_{10}$ (PFU/mL) = 5.34–5.62. The values in parentheses indicate percent reductions in viral titer from the working virus suspension.
***Incubation time 12 minutes, at 25 mg/mL test level. The activity may be caused by the sample, by microbial contaminant, or by a non-specific physical interaction between the particles of the sample and the virus, since the samples were not sterile filtered before assay.
****Incubation time 32 minutes, at 25 mg/mL test level for the "as is" unfractionated samples. For soluble, soluble & sterile filtered, and insoluble fractions, the test level was equivalent to 23 mg/mL of its unfractionated sample.

The data contained in Table 2 demonstrates that HHT888-4 and HHT888-5 are effective anti-EMuLV agents.

2. Anti-Human Immunodeficiency Virus Assay

This assay also contained two parts, a toxicity test and an HIV suppression test. The sample was mixed in a cell culture medium, e.g., 50 mg in 1.00 mL. The mixture was vortexed and centrifuged to separate the soluble from the insoluble. The supernate was filtered through a 0.45-$\mu$m filter and then diluted with cell culture medium to appropriate concentrations for the assay. The cell culture medium used in the assay was RPMI 1640 (pH 7.3±0.3) supplemented with 10% fetal calf serum, 2 mM glutamine, 50 U/mL penicillin and 50 $\mu$g/mL streptomycin.

The sample was tested for its cytotoxicity and/or cytostatic activity towards the target cells, human peripheral blood lymphocytes (PBLs). A lymphocyte proliferation assay was used for the toxicity test, where a 100 $\mu$L sample was incubated with 100 $\mu$L of a cell suspension of uninfected PBLs (3×$10^5$ cells) under the same conditions as the HIV suppression test. Lymphocyte proliferation was measured by a colorimetric assay (MTT-Test). See T. Mosmann, *J. Immunological Methods*, 65, 55–63 (1983). A sample concentration which results in ≧70% of the control in lymphocyte proliferation is considered to be acceptable for the HIV suppression test.

In the HIV suppression test, HIV-1 infected PBLs were cultivated in the presence of the sample for four (4) days as in the toxicity test. See H. Ruebsamen-Waigmann, et al., *J. Med Virology*, 19, 335–344 (1986). The secreted viral core protein p24 and/or viral RNA were determined as indicators for virus proliferation status on day 3 and day 4 by an HIV-1 p24 capture ELISA technique and an HIV-RNA dot blot hybridization technique, respectively. The concentration of p24 synthesized by the HIV infected cells was determined by Sandwich ELISA. A standard preparation of recombinant p24 (MicroGeneSys, USA) was used for calibration of the ELISA. See Ch. Mueller, et al., *Fresenius Z. Anal. Chem.*, 330, 352–353 (1988).

HIV-RNA synthesized in the infected cells was determined by a nucleic acid hybridization technique. Cellular RNA was prepared from the infected cells and analyzed by a dot blot hybridization technique. The hybridization solution contained the $P^{32}$-labeled DNA probe which comprised a 5.5 kilobase DNA fragment of the HIV isolate $D_{31}$. See H. v. Briesen, et al., *J. Med. Virology*, 23, 51–66 (1987). This fragment covering the gag/pol region of the virus is labeled with $P^{32}$ alpha-d CTP by oligonucleotide labeling. Plus-strand RNA transcripts derived from the gag/pol region of the viral isolate $D_{31}$ were used as the external standard for the hybridization. These "run-off" transcripts were generated by means of the T7 polymerase reaction from negatively polarized HIV-DNA under T7-promotor control. The concentration of RNA transcripts was determined spectrophotometrically. The hybridized probe was detected by autoradiography and the processed autoradiograms were evaluated densitometrically.

A positive control, a negative control, and an AZT control were conducted concurrently to assure the validity of the HIV suppression test. All tests were performed in triplicates, and 96-well round bottom microtiter plates were used for all assays.

A positive control was HIV-1 infected lymphocytes cultivated in the presence of the cell culture medium without the sample. A negative control was lymphocytes infected with a heat-inactivated virus inoculum incapable of replication. These "mockinfected" lymphocytes were cultivated and assayed in the same way as the infected cells. The amount of viral protein being present in the cultures solely due to the remaining inoculum was thus determined as the background level. The amount of viral protein p24 in the test sample and in the positive control due to viral replication was then determined by the respective p24 levels less the background level.

The amount of viral protein being present in the cultures containing the sample due to viral proliferation was compared with that in the positive control, i.e., the culture without the sample. The % suppression of HIV proliferation was determined by the difference in p24 levels between the positive control and the sample, divided by the p24 level of the positive control, and timed 100%.

The AZT control was conducted via HIV-1 infected lymphocytes that were cultivated in the presence of azidothymidine (AZT) at concentrations of 100, 10, 1 and 0.1 ng/mL, respectively. This provided an estimate of the sensitivity of the lymphocytes towards AZT, a known inhibitor of HIV-1 replication. The suppression of HIV-1 proliferation caused by AZT in a concentration of 10 ng/mL should be greater than 50% as compared to the untreated positive control.

Table 3 summarizes the cytotoxicity and the HIV suppression test results of HHT888-4 and HHT888-5, as well as the AZT controls. Both herb mixtures were active in suppressing HIV proliferation in infected human lymphocytes at 2.5–5.0 mg/mL, but not at 50 $\mu$g/mL (50–100 times diluted). The AZT controls from all sets exhibited the expected activities and thus assured the validity of the tests.

TABLE 3

Anti-HIV Activities of HHT888-4 and HHT888-5

| Sample | Test Concentration | Cytotoxicity* | HIV Suppression | | | |
|---|---|---|---|---|---|---|
| | | | p24 | | RNA | |
| | | | Day 3 | Day 4 | Day 3 | Day 4 |
| HHT888-4 | 2.5 mg/mL | >46% | 100% | 100% | 100% | 100% |
| | 50 g/mL | 85% | 1% | 6% | — | — |
| HHT888-5 | 5.0 mg/mL | 75% | 100% | 97% | 99% | 100% |
| | 50 g/mL | 86% | 0% | 12% | — | — |
| AZT | 100 ng/mL | — | 99–100% | 100% | — | — |
| | 10 ng/mL | — | 85–98% | 77–96% | — | — |
| | 1 ng/mL | — | 20–39% | 8–12% | — | — |
| | 0.1 ng/mL | — | 0% | 0–3% | — | — |

*Percent proliferation of control. HHT888-4 was 46% at 5.0 mg/mL. Both HHT888-4 and HHT888-5 were cytotoxic (<50% of control) at 25 mg/mL level.

At 2.5–5.0 mg/mL of HHT888 to 4 and HHT888 to 5, HIV proliferation in infected human lymphocytes was essentially completely suppressed: 97 to 100% suppression based on viral protein p24 and 99 to 100% suppression based on viral RNA determined on both day 3 and day 4 after treatment. The anti-HIV activity at 50 μg/mL was negligible, 0 to 12% suppression for both herb mixtures. The activities could not be attributed to insoluble particulates since they were filtered out by a 0.45-μm filter before the assay and the activities were not due to cytotoxicity. Repeat tests on three lots of HHT888-4 showed 100% suppression at 2.5 mg/mL on both day 3 and day 4 with acceptable cytotoxicity (71 to 100% of control proliferation). Repeat tests on three lots of HHT888 to 5 at 2.5 mg/mL showed 93–98% suppression on day 3 and 89 to 99% suppression on day 4 with acceptable cytotoxicity (85 to 91% of control proliferation). Results of the repeat experiments are shown in Table 4.

It is noted that Lot 3 of HHT888-4 or HHT888-5 was prepared by mixing the respective single-herb components at equal proportion by weight. Lot 3 of HHT888-5 was composed of nine (9) single-herb components, excluding No.5(10) and No.5(11).

Water extracts of HHT888-4 and HHT888-5 (E to E2) from one to two lots were further tested to see whether the active components were extractable by water. Water extracts of HHT888-4 and 5 were prepared by extracting 5 g of the powder with 25 mL of MilliQ purified water twice. Each water suspension was vortexed for 1 minute, stood for 5 minutes, and vortexed again for 1 minute to facilitate the extraction. The extract was separated from the insoluble by centrifuge at 1,000–2,000 rpm for 20 minutes. The supernate was transferred into a clean preweighed 50-mL centrifuge tube, freeze dried, weighed, and tested for anti-HIV activity.

The percent weight of material extracted was 17.3% for the first 25 mL extract and 10.8% for the second 25 mL

TABLE 4

Anti-HIV Activities of HHT888-4 and HHT888-5 and their Water Extracts

| Sample | Lot | % Weight | Test Concentration | Cytotoxicity* | HIV Suppression** | |
|---|---|---|---|---|---|---|
| | | | | | Day 3 | Day 4 |
| HHT888-4 | 1 | 100% | 2.5 mg/mL | >46% | 100% | 100% |
| | | | 2.5 mg/mL | 98% | 100% | 100% |
| | | | 0.05 mg/mL | 85% | 1% | 6% |
| | 2 | 100% | 2.5 mg/mL | 100% | 100% | 100% |
| | 3*** | 100% | 2.5 mg/mL | 71–79% | 100% | 100% |
| HHT888-4-E1 | 2 | 17% | 1.0 mg/mL | 98% | 100% | 96% |
| E2 | 2 | 11% | 1.0 mg/mL | 96% | 100% | 87% |
| E | 2 | 28% | 1.0 mg/mL | 47% | 100% | 100% |
| | | | 0.5 mg/mL | 78% | 100% | 100% |
| | 4 | 27 ± 1%**** | 1.0 mg/mL | 72% | 100% | 100% |
| | | | 1.0 mg/mL | 100% | 100% | 93% |
| | | | 0.1 mg/mL | 97% | 34% | 12% |
| | | | 0.02 mg/mL | 82% | 23% | 2% |
| HHT888-5 | 1 | 100% | 5.0 mg/mL | 75% | 100% | 97% |
| | | | 2.5 mg/mL | 89% | 93% | 91% |
| | | | 0.05 mg/mL | 86% | 0% | 12% |
| | 2 | 100% | 2.5 mg/mL | 91% | 94% | 89% |
| | 3*** | 100% | 2.5 mg/mL | 44–85% | 98% | 99% |
| | | | 0.5 mg/mL | 52–100% | 0% | 0% |
| HHT888-5-E | 2 | 19% | 1.0 mg/mL | 91% | 71% | 26% |

*Toxicity in percent of control proliferation.
**HIV suppression based on viral protein p24 levels.
***Composite of respective single herb components at equal proportions. No.5(10) and No.5(11) were not included in Lot 3 of HHT888-5.
****Based on two (2) runs.

extract of HHT888-4 (Lot 2). That was 14.2% for the first 25 mL extract and 4.6% for the second 25 mL extract of HHT888-5 (Lot 2). The first (E1), the second (E2) and the combined (E) extracts of HHT888-4 (Lot 2) were tested for anti-HIV activity. All the other extracts were tested with the first and the second extracts combined. The results are also set forth in Table 4.

All three lots of each of the herb mixtures were very active, 100% suppression at 2.5 mg/mL for HHT888 to 4 and 89–100% suppression at 2.5 to 5.0 mg/mL for HHT888 to 5. The $IC_{50}$ was between 0.05 to 2.5 mg/mL for HHT888 to 4 and between 0.5 to 2.5 mg/mL for HHT888 to 5. $IC_{50}$ is the concentration of the test substance at which would cause 50% suppression of the viral proliferation.

The water extract of HHT888-4 showed very good activity: 93 to 100% suppression at 0.5 to 1.0 mg/mL. The first (E1) and the second water extract (E2) of Lot 2 exhibited comparable activities: 100% suppression on day 3 and 87 to 96% suppression on day 4 at 1.0 mg/mL. The $IC_{50}$ of the water extract of HHT888 to 4 was between 0.1–0.5 mg/mL.

The water extract of HHT888-5 (Lot 2) exhibited a substantially lower activity: 71% suppression on day 3 which dropped to 26% suppression on day 4 at 1.0 mg/mL. The main active component apparently stayed behind in the insoluble fraction and was not as easily extracted by water as that of HHT888-4 under the aforementioned conditions. It is noted that the water extract of HHT888-5 (Lot 2) constituted 19% by weight of the herb mixture. The test concentration of the water extract of HHT888-5 (or HHT888-5-E) at 1.0 mg/mL is equivalent to 5.3 mg/mL of HHT888-5 itself. HHT888-5 was tested very active at both 2.5 mg/mL (93 to 98% suppression on day 3 and 89 to 99% on day 4) and 5.0 mg/mL (100% suppression on day 3 and 97% on day 4).

The above results clearly demonstrated that both HHT888-4 and HHT888-5 and their water extracts have in vitro antiretroviral activities, more specifically anti-EMuLV and anti-HIV activities. HHT888-5 has also been shown to be efficacious in treating hepatitis B virus carriers.

EXAMPLE 5

Antiretroviral Testing of Individual Single-herb Herbal Medicines

In this experiment, the individual single-herb components of HHT888-4 and HHT888-5 were tested for anti-HIV activity. Table 5 sets forth the test results.

TABLE 5

Anti-HIV Activities of Single-herb Components of HHT888-4 and HHT888-5

| Sample | Lot | Test Concentration | Cytotoxicity* | HIV Suppression** Day 3 | Day 4 |
|---|---|---|---|---|---|
| No. 4(1)*** | 1 | 2.5 mg/mL | 98% | 73% | 50% |
| No. 4(2) | 1 | 2.5 mg/mL | 74–84% | 92% | 94% |
| No. 4(3) | 1 | 2.5 mg/mL | 75–78% | 100% | 100% |
| No. 4(4) | 1 | 2.5 mg/mL | 74–100% | 100% | 100% |
| No. 4(5) | 1 | 2.5 mg/mL | 41–79% | 98% | 92% |
|  |  | 0.5 mg/mL | 47–100% | 0% | 0% |
| No. 5(1)*** | 1 | 2.5 mg/mL | 98% | 73% | 50% |
| No. 5(2) | 1 | 2.5 mg/mL | 73–87% | 18% | 29% |
| No. 5(3) | 1 | 2.5 mg/mL | 89–100% | 0% | 0% |
| No. 5(4) | 1 | 2.5 mg/mL | 64% | 100% | 100% |
|  |  | 1.0 mg/mL | 69–91% | 0% | 0% |
| No. 5(5) | 1 | 2.5 mg/mL | 80–84% | 93% | 93% |

TABLE 5-continued

Anti-HIV Activities of Single-herb Components of HHT888-4 and HHT888-5

| Sample | Lot | Test Concentration | Cytotoxicity* | HIV Suppression** Day 3 | Day 4 |
|---|---|---|---|---|---|
| No. 5(6) | 1 | 2.5 mg/mL | 94–100% | 0% | 0% |
| No. 5(7) | 1 | 2.5 mg/mL | 90–100% | 50% | 38% |
| No. 5(8) | 1 | 2.5 mg/mL | 32–59% | 100% | 100% |
|  |  | 0.5 mg/mL | 65–100% | 0% | 0% |
| No. 5(9) | 1 | 0.5 mg/mL | 24–78% | 0% | 0% |
| No. 5(10) | 1 | 2.5 mg/mL | 100% | 65% | 0% |
| No. 5(11) | 1 | 2.5 mg/mL | 100% | 92% | 74% |

*Toxicity in percent of control proliferation.
**HIV suppression based on viral protein p24 levels.
***No. 4(1) = No. 5(1)

All five (5) single-herb components of HHT888-4 exhibited anti-HIV activities with various degrees: 73 to 100% suppression on day 3 and 50 to 100% suppression on day 4 at 2.5 mg/mL. No.4(3) and No.4(4) exhibited the best activity: 100% suppression at 2.5 mg/mL on both day 3 and day 4. No.4(2) and No.4(5) were the next: 92 to 98% suppression on day 3 and 92 to 94% suppression on day 4 at 2.5 mg/mL. No.4(1) exhibited a moderate activity: 73% suppression on day 3 and 50% suppression on day 4 at 2.5 mg/mL. No.4(5) exhibited a slight cytotoxicity (41 to 79% of control proliferation) which was likely to contribute to the observed activity with an $ID_{50}$ between 0.5 and 2.5 mg/mL.

Three (3) of the eleven (11) single-herb components of HHT888-5: No.5(4), No.5(5), and No.5(8) exhibited very good activities, 93 to 100% suppression of HIV proliferation on both day 3 and day 4 at 2.5 mg/mL. No.5(11) was the next: 92% suppression on day 3 and 74% suppression on day 4 at 2.5 mg/mL. Again, No.5(1), which was the same as No.4(1), had a moderate activity: 73% suppression on day 3 and 50% suppression on day 4 at 2.5 mg/mL. No.5(2) and No.5(7) exhibited only marginal activities: 18 to 50% suppression on day 3 and 29–38% suppression on day 4 at 2.5 mg/mL. No.5(10) exhibited a very slight activity: 65% suppression on day 3 which dropped to 0% on day 4 at 2.5 mg/mL. The remaining three (3) single-herb components, No.5(3), No.5(6), and No.5(9) exhibited no activity at 0.5 to 2.5 mg/mL. No.5(9) was not tested at 2.5 mg/mL level because of its cytotoxicity: already 24–78% of control proliferation at 0.5 mg/mL.

Although No.5(4) and No.5(8) appeared to be slightly more active than No.5(5) (100% vs. 93% suppression at 2.5 mg/mL), their activities might be partially due to cytotoxicity (32 to 64% of control proliferation at 2.5 mg/mL). This was supported by the loss of activity (0% suppression) when tested at lower levels, 0.5 to 1.0 mg/mL, where the cytotoxicity was lower and more acceptable to the assay.

EXAMPLE 6

Anti-HIV Testing of Medicinal Plant

The source plant of the single-herb herbal medicine No.5(5), *Aeginetia indica*, was obtained from a local herbal store in Taiwan and tested for its anti-HIV activity. This was to see whether the activity can be reproduced in the herbal medicine prepared directly from its source plant, instead of being obtained from the commercial source.

The whole plant was washed with cold water, dried, comminuted, and extracted with boiling water as described in Example 2. The aqueous solution was separated from the plant material by filtration. The aqueous solution was then reduced in volume by heating. The concentrate was spray dried and absorbed onto powdered material of the same plant material and thus was prepared the herbal medicine in powder form, designated hereinafter as raw No.5(5).

The powdered herbal medicine prepared from *Aeginetia indica*, or raw No.5(5), was extracted with water at ambient temperature. Two (2) 5.00 g samples were each extracted twice with about 40 mL of water each time in a separate 50-mL plastic centrifuge tube by vortexing for one (1) minute, standing for ten (10) minutes, and vortexing again for one (1) minute. The tubes were centrifuged at 1500 rpm for twenty (20) minutes to separate the extracts from the insoluble residues. The extracts were filtered through a Whatman No.4 filter paper, freeze dried or nitrogen dried, and weighed.

The above extraction of the raw No.5(5) with water (pH ~5.1) was repeated and the pH of the first extract was measured to be 5.7. The first and the second extracts were respectively separated from the residue, air dried, and weighed. The percent weight of the extractable was determined to be 18.7±2.8% (n=2).

The first water extract of the raw No.5(5) was tested for anti-HIV activity and found to be active, 91% suppression on day 3 and 97% suppression on day 4 at 1.0 mg/mL. Cytotoxicity test showed that the extract was not cytotoxic at this level, 99% of control proliferation.

EXAMPLE 7

Treatment of Hepatitis C Patients

HHT888-5 has been demonstrated to be effective and safe in treating HBV infections in humans. That means, the active principle or principles of HHT888-5 must be bioavailable in humans through oral administration to cause the decrease of HBV in those patients treated, as indicated by the decrease of their HBV surface antigen (HBsAg) exhibited in Example 3. In addition, Hozumi et al. provided examples in U.S. Pat. No. 5,411,733 to support the belief that substances exhibiting antiviral activity in vitro also possess antiviral activity in vivo as described in the Prior Art section. It is therefore logical to believe that HHT888-4 or HHT888-5 and their water extracts or active principles should also be effective for treating HIV infections in humans.

To test this belief, six (6) of the most anti-HIV active single-herb components of HHT888-4 and HHT888-5 were selected to treat hepatitis C patients caused by HCV infections. The logic is that both HCV and HIV are retroviruses. Viral hepatitis C tends to become a chronic disease and is therefore more suitable for the test of the treatment. If the treatment works for patients infected with HCV, it will also work for patients infected with HIV. Example 7 clearly demonstrates the validity of this belief.

Six (6) of the most anti-HIV active single-herb components of HHT888-4 and HHT888-5 were selected and mixed to treat hepatitis C patients caused by HCV infections. The six (6) single-herb herbal medicines selected were No.4(2), No.4(3), No.4(4), No.5(4), No.5(5), and No.5(8). No.4(5) was not included although it exhibited a very good activity, because it was learned that the herb might have a certain unconfirmed toxicity.

The six (6) single-herb herbal medicines were obtained from a commercial source and were manufactured following good manufacture practice (GMP) guidelines. They were mixed according to the desired ratio in various combinations and thus the herb mixture HHT888-45 was prepared as described in Example 1. Patients' consents were obtained before the initiation of treatment.

Patients were instructed to take the herb mixture three (3) times a day, 2.7 to 5.7 g each time. Unit dosages of the herb mixture HHT888-45 were prepared in individual packets. Each unit dose packet (2.7 to 5.7 g) of the herb mixture was mixed with warm water and taken orally. All patients were treated with HHT888-45 containing No.4(3), No.4(4), No.5 (4), and No.5(5). No.5(8) or No.4(2) or both were added in HHT888-45 for the treatment of some patients at the very beginning or during the course of the treatment to enhance the effectiveness of the treatment.

During the course of the treatment, the daily dose of No.4(3), No.4(4), No.5(4), and No.5(5) varied from two (2) to three (3) grams each. The daily dose of No.5(8) also varied from two (2) to three (3) grams when used. The daily dose of No.4(2) varied from 1.5 to two (2) grams when used. The dose was varied according to the progress of the disease.

Seven (7) viral hepatitis C patients were treated. Their serum liver enzymes, SGOT and SGPT, were determined from time to time by a local clinical laboratory during the course of the treatment to monitor the progress of the disease. The SGOT and SGPT were determined using an enzyme assay. See (1) *Instruction of Kyokuto TA-E Transaminase Assay Reagents*, Permit No. (62AM)0885, Kyokuto Pharmaceutical Industry Co., Ltd., Tokyo, Japan, 1994; (2) *Instruction of Yatrozyme TA-Lq Transaminase-assay Reagent Solution* (Enzyme Assay), Commodity No. 817245 (RM163-K), Yatron Co., Ltd., Diayatron Co., Ltd., Tokyo, Japan; and (3) U. Lippi & G Guidi, *Clin. Chem. Acta.*, 28, 431–437 (1970).

The levels of serum GOT and GPT closely correlate with the degree of cellular injury in the liver. These tests are widely used in the diagnosis of liver diseases and as an indicator of the liver function. The normal range for SGOT is 8-40 units/mL and that for SGPT is 5-35 units/mL. Elevated SGOT and SGPT levels usually indicate compromised liver functions.

The results of HHT888-45 treatment are shown in Table 6. All seven (7) patients treated had their serum liver enzymes returned from elevated levels (SGOT from 48 to 166 unit/mL and SGPT from 41 to 291 unit/mL) to essentially normal range (SGOT from 8 to 40 unit/mL and SGPT from 5 to 35 unit/mL) after 17 to 178 days of treatment. Thus, the liver functions of the patients were returned to normal after consumption of the inventive composition.

TABLE 6

Clinical Effect Of HHT888-45* On Type C Hepatitis Patients

| Patient | SGOT**, unit/mL | | SGPT**, unit/mL | | Duration |
|---|---|---|---|---|---|
| | Before | After | Before | After | (days) |
| 1 | 112 | 53 | 238 | 146 | 3 |
| | | 30 | | 35 | 64 |
| | | 16 | | 18 | 77 |
| 2 | 81 | 35 | 103 | 62 | 9 |
| | | 41 | | 61 | 20 |
| | | 46 | | 67 | 29 |
| | | 32 | | 56 | 37 |
| | | 21 | | 43 | 53 |
| | | 24 | | 50 | 70 |
| | | 23 | | 43 | 85 |
| | | 28 | | 55 | 102 |

TABLE 6-continued

Clinical Effect Of HHT888-45* On Type C Hepatitis Patients

| Patient | SGOT**, unit/mL Before | SGOT**, unit/mL After | SGPT**, unit/mL Before | SGPT**, unit/mL After | Duration (days) |
|---|---|---|---|---|---|
| | | 23 | | 44 | 117 |
| | | 23 | | 29 | 178 |
| 3 | 117 | 96 | 179 | 123 | 8 |
| | | 75 | | 74 | 19 |
| | | 66 | | 69 | 26 |
| | | 47 | | 51 | 34 |
| | | 55 | | 48 | 42 |
| | | 42 | | 45 | 50 |
| | | 48 | | 40 | 70 |
| | | 38 | | 32 | 79 |
| | | 30 | | 26 | 88 |
| 4 | 48 | 32 | 71 | 65 | 56 |
| | | 30 | | 55 | 70 |
| | | 21 | | 37 | 87 |
| 5 | 83 | 64 | 67 | 54 | 8 |
| | | 58 | | 46 | 14 |
| | | 56 | | 40 | 22 |
| | | 42 | | 34 | 29 |
| | | 38 | | 28 | 36 |
| 6 | 166 | 106 | 291 | 206 | 2 |
| | | 71 | | 121 | 16 |
| | | 51 | | 81 | 22 |
| | | 57 | | 89 | 29 |
| | | 36 | | 45 | 45 |
| | | 31 | | 36 | 50 |
| | | 28 | | 37 | 58 |
| | | 22 | | 29 | 64 |
| | | 28 | | 32 | 71 |
| | | 25 | | 27 | 85 |
| | | 36 | | 28 | 103 |
| | | 23 | | 27 | 113 |
| | | 23 | | 22 | 163 |
| 7 | 30 | 28 | 41 | 42 | 9 |
| | | 29 | | 32 | 17 |

*Comprising mainly Nos. 4(3), 4(4), 5(4) and 5(5), and occasionally 4(2) and 5(8).
**SGOT = serum glutamine oxalacetate transferase; normal range = 8–40 unit/mL.
SGPT = serum glutamine pyruvate transferase; normal range = 5–35 unit/mL.

The results clearly demonstrate that the herb mixture HHT888-45 is effective in treating hepatitis C patients. To accomplish that, the causative HCV needs to be eradicated or reduced to a tolerable level. Since HHT888-45 components have demonstrated very strong anti-HIV in vitro activity and several of the components have demonstrated efficacy in reducing HBV in carriers, the herb mixture will therefore be effective in treating patients infected with HIV and HBV.

It is therefore an aspect of this invention that the antiviral herbal medicines including the herb mixtures according to this invention and their single-herb components at various proportions and effective doses are effective in treating hepatitis C, hepatitis B, and other retroviral diseases, such as AIDS.

Since a precise chemical identification and pharmacological mechanism of the compositions of this invention have not yet been elucidated, it is possible that the antiviral activity may be due to a single herbal component, a combination of components or the biological metabolite or derivative thereof. The following Examples investigate the chemical identification of the active components set forth in this application.

EXAMPLE 8

Fractionation of Active Single-Herb Components

The three most anti-HIV active single-herb components of HHT888-5: No.5(4), No.5(5) and No.5(8) were fractionated by water extraction, C18 solid-phase-extraction (SPE) column liquid chromatography (C18-SPE-LC) and C18 column high-performance liquid chromatography (C18-HPLC). The herb mixture HHT888-4 was also fractionated concurrently for comparison. The purpose was to identify the active compound or compounds of each anti-HIV active herbal medicines or medicinal herbs.

1. Water Extraction

The single-herb herbal medicines No.5(4), No.5(5) and No.5(8) and the herb mixture HHT888-4 were extracted twice with water at ambient temperature (about 25° C.) with 8 to 10 mL of water per gram of sample (e.g., 5 g powder with 40 mL water and 50 g powder with 500 mL water) each time. The water suspension was stirred for fifteen (15) minutes or vortexed for one (1) minute, stood for ten (10) minutes and vortexed again for one (1) minute. The water extract was separated from the insolubles by centrifuge at 1,500 rpm for twenty (20) minutes and filtered through a Whatman No. 4 filter paper.

2. C18-SPE-LC

Each water extract was fractionated by C18-SPE column liquid chromatography. A ten (10) mL aliquot of the extract was loaded onto a 10-g ISOLUTE C18(EC)-SPE column (from International Sorbent Technology, Ltd., Hengoed, Mid-Glamorgan, UK or Jones Chromatography, Lakewood, Colo., USA) which was preconditioned with 50 mL ethanol and 100 mL water. The SPE column (2.6 cm inside diameter by 2.7 cm length, plus 60 mL of reservoir) was packed with 10 g of end-capped (EC) C18 sorbent particles with an average particle diameter of 61 $\mu$m and carbon loading of 19%.

The loaded column was eluted in sequence and by gravity with 90 mL water, 100 mL ethanol, 100 mL 1% HCl in ethanol, and 50 mL 0.1% HCl in ethanol/water at 10/90, v/v. Eluate was collected in 50-mL samples. The water eluates were either freeze-dried in a glass flask or air-dried in plastic weighing dishes. The ethanol, acidic ethanol, and acidic ethanol/water eluates were air-dried respectively in plastic weighing dishes. The air-dried acidic ethanol (1% HCl in ethanol) and acidic ethanol/water (0.1% HCl in ethanol/water at 10/90, v/v) eluates were redissolved in 1% HCl/ethanol and water, respectively; then transferred into 4-mL WISP vials and dried again under nitrogen. The dried fractions of the first 50 mL water eluate (A), the first 50 mL ethanol eluate (B), the first 50 mL 1% HCl/ethanol eluate (C), and the 50 mL 0.1% HCl/10% ethanol/90% water eluate (D) were tested for anti-HIV activities as previously described. The results are shown in Table 7.

TABLE 7

Anti-HIV Activities Of C18-SPE-LC Fractions Of HHT888-4E, No.5(4)E, No.5(5)E and No.5(8)E

| Water Extract | C18-SPE-LC Fraction** | % Weight*** | Test Level | Toxicity**** | Anti-HIV Activity* Day 3 | Day 4 |
|---|---|---|---|---|---|---|
| HHT888-4E | A | 70.0 ± 4.5% | 0.7 mg/mL | 50–73% | 98% | 61% |
| | B | 18.5 ± 1.3% | 0.2 mg/mL | 21–95% | 100% | 87% |
| | C | 6.7 ± 2.7% | 0.1 mg/mL | 98% | 95% | 85% |
| | D | 2.1 ± 1.5% | 0.1 mg/mL | 100% | 42% | 0% |
| No.5(4)E | A | 78.6 ± 7.6% | 1.0 mg/mL | 78% | 99% | 14% |
| | | | 0.2 mg/mL | 76–97% | 90% | 20% |
| | B | 14.6 ± 3.9% | 0.1 mg/mL | 68% | 80% | 2% |
| | | | 0.05 mg/mL | >68% | 63% | 0% |
| | C | 4.1 ± 0.3% | 0.1 mg/mL | 91% | 49% | 0% |
| | D | 3.0 ± 1.5% | 0.1 mg/mL | 96% | 19% | 0% |
| No.5(5)E | A | 73.9 ± 7.9% | 1.0 mg/mL | 98% | 100% | 100% |
| | | | 0.3 mg/mL | 97–98% | 100% | 94% |
| | | | 0.3 mg/mL | 85–90% | 99% | 99% |
| | | | 0.1 mg/mL | 85% | 91% | 86% |
| | B | 14.6 ± 4.1% | 0.1 mg/mL | 48% | 98% | 90% |
| | | | 0.07 mg/mL | >48% | 99% | 41% |
| | C | 8.6 ± 1.8% | 0.1 mg/mL | 99% | 96% | 96% |
| | D | 2.5 ± 1.7% | 0.1 mg/mL | 96% | 25% | 0% |
| No.5(8)E | A | 43.6 ± 2.6% | 0.5 mg/mL | 70% | 93% | 54% |
| | | | 0.3 mg/mL | 70–100% | 96% | 5% |
| | B | 53.7 ± 5.0% | 0.3 mg/mL | 24–68% | 100% | 100% |
| | | | 0.1 mg/mL | 68% | 88% | 30% |
| | C | 2.2 ± 0.9% | 0.1 mg/mL | 100% | 49% | 0% |
| | D | 1.6 ± 0.5% | 0.1 mg/mL | 95% | 14% | 0% |

*% suppression of HIV proliferation based on viral protein p24 levels.
**A = Water Eluate; B = Ethanol Eluate; C = 1% HCl/Ethanol Eluate; D = 0.1% HCl/10% Ethanol/90% Water Eluate.
***Determined from three to five runs.
****Toxicity in percent of control proliferation.

Table 7 sets forth the cytotoxicity and anti-HIV activity test results of C18-SPE-LC fractions A, B, C and D of HHT888-4E, No.5(4)E, No.5(5)E and No.5(8)E.

The average % weight and the standard deviation of each C18-SPE-LC fraction for the water extract (E) of each sample determined from three (3) to five (5) runs are also shown in Table 7. The sample load per column per run was 199 to 205 mg for HHT888-4E, 94 to 95 mg for No.5(4)E, 124 to 130 mg for No.5(5)E, and 165 to 178 mg for No.5(8)E on dry weight basis.

The results show that the water eluate (A) and the 1% HCl/ethanol eluate (C) fractions of No.5(5)E and the 1% HCl/ethanol eluate fraction (C) of HHT888-4E are the most active ones (91 to 96% suppression of HIV proliferation on day 3 and 85 to 96% suppression on day 4 at 0.1 mg/mL) and noncytotoxic (85 to 99% of control). Air drying did not affect the activity of the water eluate fraction (A) of No.5 (5)E. An air-dried No.5(5)E-A exhibited an activity of 99% suppression on both day 3 and day 4 at 0.3 mg/mL and 91% suppression on day 3 and 86% suppression on day 4 at 0.1 mg/mL. As a comparison, a freeze-dried No.5(5)E-A exhibited an activity of 100% suppression on both day 3 and day 4 at 1.0 mg/mL and 100% suppression on day 3 and 94% suppression on day 4 at 0.3 mg/mL.

The ethanol eluate fractions (B) of HHT888-4E, No.5(5) E, and No.5(8)E also exhibited good anti-HIV activities: 100% suppression on day 3 and 87% suppression on day 4 at 0.2 mg/mL for HHT888-4E, 98% suppression on day 3 and 90% suppression on day 4 at 0.1 mg/mL for No.5(5)E, and 100% suppression on both day 3 and day 4 at 0.3 mg/mL for No.5(8)E. However, the observed activities may be attributed partly to the cytotoxicity: 21 to 95% of control proliferation for HHT888-4, 48% for No.5(5)E, and 24 to 68% for No.5(8)E. This hypothesis was supported by the significant decrease of the activity when the sample concentration was lowered to a less cytotoxic level. For example, the activity decreased from 90% to 41% inhibition on day 4 for No.5(5)E-B when its concentration was decreased from 0.1 to 0.07 mg/mL. The activity decreased from 100% to 30% inhibition on day 4 for No.5(8)E-B when its concentration was decreased from 0.3 to 0.1 mg/mL.

The water eluate fractions (A) of HHT888-4E and No.5 (8)E exhibited moderate anti-HIV activity: 98% suppression on day 3 and 61% suppression on day 4 at 0.7 mg/mL for HHT888-4E and 93% suppression on day 3 and 54% suppression on day 4 at 0.5 mg/mL for No.5(8)E. However, the activity may be partly attributed to cytotoxicity, which was 50 to 73% for HHT888-4E and 70% for No.5(8)E. The activity of No.5(8)E-A decreased from 54% to 5% on day 4 when the concentration decreased from 0.5 to 0.3 mg/mL where the cytotoxicity level (70–100% of control) was more acceptable.

The water eluate fraction (A) of No.5(4)E was marginally active: 90 to 99% suppression on day 3 and 14 to 20% suppression on day 4 at 0.2 to 1.0 mg/mL, respectively. The ethanol eluate fraction (B) of No.5(4)E, 1% HCl/ethanol eluate fractions (C) of Nos. 5(4)E and 5(8)E, and 0.1% HCl/10% ethanol/90% water eluate fractions (D) of all four samples were essentially not active at the levels tested: 14 to 80% suppression on day 3 and 0 to 2% suppression on day 4 at 0.05 to 0.1 mg/mL.

Additional runs of C18-SPE-LC fractionation of No.5 (5)E were conducted to produce more No.5(5)E-A and C fractions for further evaluation. Water extract (E) of No.5(5) was either loaded directly (10 mL per column), or was freeze-dried or air-dried first, redissolved in water (20 to 80 mg/mL), and then loaded (5 mL per column) for the fractionation. The overall % weight distribution of each fraction from these runs of No.5(5)E was: A=74.2± 6.0%, B=12.2±4.0%, C=8.2±2.1%, and D=2.1±0.9%. These values are in good agreement with those shown in Table 7.

3. C18-HPLC

The above air-dried No.5(5)E-A was further fractionated by C18-HPLC. A 500.9 mg sample was dissolved in 5.00 mL water which was then centrifuged at 1500 rpm for twenty (20) minutes to separate the solution from the insolubles. The supernate was filtered through a 0.45-$\mu$m filter to remove any insoluble residues and was designated the water soluble fraction (WS). The precipitate was extracted with 5.00 mL of water three more times and nitrogen dried as the water insoluble fraction (WI). The water soluble fraction (WS) was fractionated by a gradient HPLC using a Rainin Dynamax C18 preparatory column (21.4×250 mm, 5 $\mu$m particles) and the following conditions:

| Flow rate: | 9.00 mL/min | |
|---|---|---|
| Injection Volume: | 200 $\mu$L | |
| Detection: | UV 214 nm at 2.00 AUFS | |
| Gradient: | Time | Acetonitrile/Water |
| | 0–10 min | 2/98 |
| | 10–25 min | 2/98 → 98/2 (linear) |
| | 25–30 min | 98/2 |
| | 30–35 min | 98/2 → 2/98 (linear) |
| | 35–70 min | 2/98 |

Fractions were collected at 2.5 min intervals. A total of 28 fractions were collected at 22.5 mL for each fraction. Table 8 indicates that certain fractions were pooled before conducting the assay.

Each of the above nitrogen dried C18-HPLC fractions was tested for anti-HIV activity at a concentration equivalent to 0.33 mg/mL of the starting material, i.e., the water soluble fraction (WS) of the air-dried No.5(5)E-A. The purpose was to identify the active fraction or fractions of the air-dried No.5(5)E-A which tested very active: 99% suppression of HIV proliferation at 0.3 mg/mL (see Table 7). At the concentration equivalent to 0.33 mg/mL of the starting material, any active fraction was expected to also have a very good activity of 99% suppression. The first water extract (WS) and the precipitate (WI) of the air-dried No.5 (5)E-A were also tested concurrently at 0.33 mg/mL. Table 8 sets forth the results. The % weight of each fraction is included and Fraction 3 contains the main peak.

TABLE 8

Anti-HIV Activities Of Water Soluble And Insoluble Fractions Of Air-Dried No. 5(5)E-A And The HPLC Fractions Of The Water Soluble Fraction

| No. 5(5)B-A Fractions* | % Weight** | Toxicity*** | Anti-HIV Activity**** Day 3 | Day 4 |
|---|---|---|---|---|
| Water Insoluble (WI) | 10.3% | 100% | 100% | 100% |
| Water Soluble (WS) | 86.0% | 100% | 86% | 63% |
| WS-HPLC-F1 & 2 | 6.8% | 86% | 0% | 4% |
| WS-HPLC-F3 | 109% | 73% | 0% | 1% |
| WS-HPLC-F4 | 2.7% | 93% | 8% | 0% |
| WS-HPLC-F5 | 2.0% | 100% | 0% | 0% |
| WS-HPLC-F6 | 0.7% | 100% | 15% | 0% |
| WS-HPLC-F7 | <0.2% | 100% | 46% | 0% |
| WS-HPLC-F8 | 3.0% | 100% | 0% | 0% |
| WS-HPLC-F9 | <0.2% | 100% | 0% | 0% |
| WS-HPLC-F10 | <0.2% | 87% | 0% | 1% |
| WS-HPLC-F11 & 12 | 0.7% | 91% | 1% | 1% |
| WS-HPLC-F13 & 14 | 10% | 96% | 0% | 0% |
| WS-HPLC-F15 & 16 | 7.0% | 89% | 18% | 0% |

TABLE 8-continued

Anti-HIV Activities Of Water Soluble And Insoluble Fractions Of Air-Dried No. 5(5)E-A And The HPLC Fractions Of The Water Soluble Fraction

| No. 5(5)B-A Fractions* | % Weight** | Toxicity*** | Anti-HIV Activity**** Day 3 | Day 4 |
|---|---|---|---|---|
| WS-HPLC-F17 & 18 | 1.5% | 77% | 25% | 3% |
| WS-HPLC-F19 to 28 | 1.2% | 80% | 0% | 0% |

*WI and WS were water insoluble and soluble fractions of the air-dried No. 5(5)E-A. WS-HPLC-F1 to 28 were the HPLC fractions of WS.
**% Weight of the starting material (WS)
***Toxicity in % of control proliferation.
****Activity in % supppression of HIV proliferation based on viral protein p24 level. The test levels for WI and WS of the air-dried No. 5(5)E-A were both 0.33 mg/mL. The test levels for all HPLC fractions of WS were equivalent to 0.33 mg/mL of the starting material WS.

Table 8 shows that fraction WS-HPLC-F3 contained the most material, however, it was essentially not active in the anti-HIV assay.

These results are very surprising. All C18-HPLC fractions tested were essentially inactive, 0 to 4% suppression on day 3 and 0–4% suppression on day 4. The water soluble fraction (WS) also showed a significantly lower activity (86% suppression on day 3 and 63% suppression on day 4 at 0.33 mg/mL) than expected. This type of activity loss during separation and purification of active components from medicinal plants has been widely experienced by others, mostly attributing to the loss of synergistic effects when the compounds are separated from their matrix.

Our results indicated that the active component was surprisingly left behind in the water insoluble fraction (WI), instead of in the water soluble fraction (WS) as originally expected. The insoluble fraction tested very active, 100% suppression on both day 3 and day 4 at 0.33 mg/mL. That means the main active component of the air-dried No.5(5) E-A is in the water insoluble fraction (WI), instead of in the soluble fraction (WS).

The active component of No.5(5)E-A was originally soluble in water since it was in the C18-SPE-LC water eluate fraction. It had to become insoluble in water during the air drying and thus remained in the water insoluble fraction. The water insoluble fraction then must have become soluble in the neutral cell culture medium for it to be tested active. This must be the case as the sample solution in the cell culture medium was centrifuged and 0.45-$\mu$m filtered to remove insoluble substances before the anti-HIV assay.

EXAMPLE 9

Identification of Active Components

1. No.5(5)E-A

The pH of the cell culture medium used to dissolve the sample for anti-HIV assay was 7.3±0.3. It was therefore hypothesized that the active component of No.5(5)E-A was soluble in neutral aqueous solution, like the cell culture medium, but became acidified and thus insoluble upon exposure to the atmosphere containing HCl vapor during the air drying in a hood together with other C18-SPE-LC fractions that contained HCl. That means the acid form of the active component of No.5(5)E-A would be insoluble in water and precipitate when acidified. No.5(5)E-A is the C18-SPE-LC water eluate fraction of No.5(5) water extract.

To test the hypothesis, we tested the solubility of the above active precipitate (WI) from No.5(5)E-A in various solvents. The precipitate was slightly soluble in water and acidic ethanol solutions, such as 1% HCl in ethanol and 0.1% HCl in ethanol/water (10/90, v/v), and formed very light to light yellow solutions with dark brown precipitates. It was not soluble in methanol, acetone, and 1% hydrochloric acid. It was soluble but slowly in neutral phosphate buffer saline (PBS, pH 7.2) which became a dark brown solution overnight. It was rapidly and completely solubilized in 1% ammonium hydroxide solution (pH of 10.4) which quickly became a dark brown solution. This confirmed the above hypothesis that the active component was soluble in neutral or alkaline solutions but insoluble in acid solution.

Based on the solubility test, the active precipitate (WI) of No.5(5)E-A should be an acid or acids. The fact that it was not soluble in alcohols (methanol, ethanol, isopropanol), acetone, and other common organic solvents (acetonitrile, chloroform, and hexane) suggests that it is unlikely to be a simple organic acid, such as benzoic acid. The fact that it became progressively more soluble in aqueous solutions with an increase of pH indicated a transition from its acid form to a more soluble salt form.

To more definitively identify the active component of No.5(5)E-A, three water eluate fractions of No.5(5)E which were dried differently were extracted with water the same way as that of the air-dried No.5(5)E-A used for the above HPLC fractionation. One fraction was freeze-dried (FD) and two were air-dried (AD1 & AD2). AD1 and FD were prepared from the same water eluate. AD2 was the one whose activity was surprisingly found in the water insoluble fraction (WI).

Each sample was dissolved in water at 100 mg/mL and centrifuged (1,500 rpm for 20 min) to separate the soluble from the insoluble. For FD and AD1, 1.20 g of the sample was dissolved in 12.0 mL water. For AD2, 0.567 g was dissolved in 5.67 mL water. Each precipitate was extracted again with the same amount of water three more times. A 0.40 mL aliquot of each extract was nitrogen-dried and weighed. The remaining extracts were each 0.45-$\mu$m filtered, acidified with 1% HCl (e.g., 4 mL acid to 10 mL extract), and centrifuged (2,000 rpm for 20 min). The acid supernate (AS) was 0.45-$\mu$m filtered. The acid precipitate (AP) was washed with 10 mL 0.01% HCl (pH 2.82) two times and 10 mL water two times, nitrogen-dried and weighed.

Table 9 shows the pH of each water extract of the freeze dried (FD) and air dried (AD1, AD2) No.5(5)E-A's, the percent (%) weight distribution of each extract and the precipitate, acid precipitate formation of each extract, and the % weight of the combined acid precipitate from each No.5(5)E-A.

TABLE 9

Water Extracts, Water Precipitates And Acid Precipitates Of Freeze Dried (FD) And Air Dried (AD1, AD2) No. 5(5)E-A's

| No. 5 (5)E-A | Fractions* | Solution pH | % Weight | Acid Precipitation | Acid Precipitate % Weight |
|---|---|---|---|---|---|
| FD | 1st Water Extract | 5.80 | 86.8% | Yes | 8.5%** |
|  | 2nd Water Extract | 6.10 | 2.8% | Some |  |
|  | 3rd Extract | 5.79 | 0.3% | Trace |  |
|  | 4th Extract | 5.85 | <0.3% | No |  |
|  | Water precipitate | — | 0.9% | — |  |
| AD1 | 1st Water Extract | 4.83 | 84.0% | Yes | 8.3%** |
|  | 2nd Water Extract | 5.14 | 3.8% | Some |  |
|  | 3rd Water Extract | 5.53 | 0.8% | No |  |
|  | 4th Water Extract | 5.44 | <0.3% | No |  |
|  | Water precipitate | — | 3.1% | — |  |

TABLE 9-continued

Water Extracts, Water Precipitates And Acid Precipitates Of Freeze Dried (FD) And Air Dried (AD1, AD2) No. 5(5)E-A's

| No. 5 (5)E-A | Fractions* | Solution pH | % Weight | Acid Precipitation | Acid Precipitate % Weight |
|---|---|---|---|---|---|
| AD2 | 1st Water Extract | 3.21 | 77.3 ± 3.2% | No | 0.3%*** |
|  | 2nd Water Extract | 3.51 | 6.9 ± 0.8% | No |  |
|  | 3rd Water Extract | 3.87 | 2.3 ± 1.1% | Some |  |
|  | 4th Water Extract | 3.93 | 0.3 ± 0.4% | Some |  |
|  | Water precipitate | — | 9.4 ± 1.3% | — |  |

*At 100 mg/mL of No. 5(5)E-A in water.
**Acid precipitates from the 1st and 2nd extracts combined.
***Acid precipitate from the 3rd and 4th extracts combined.

It was clearly shown that the water extracts of AD2 were more acidic (pH's 3.2 to 3.9) than those of AD1 (pH's 4.8 to 5.5) and FD (pH's 5.8 to 6.1). The AD2 sample contained more water insoluble substance (9.4%) than AD1 (3.1%) and FD (0.9%). The more acidic the water extracts the greater amount of the insoluble substance isolated.

When the water extracts were acidified, the first and second extracts of FD and AD1 formed precipitate, while those of AD2 did not. Instead, some precipitate formed in the 3rd and 4th extracts of AD2 whose original pH was 3.9. A trace precipitate was observed in the acidified 3rd extract of FD, while no precipitate was observed in the 4th extract of FD and in the 3rd and 4th extracts of AD1.

This indicated that the active precipitate was insoluble in water at pH 3.2 to 3.5, slightly soluble at pH 3.9, and became soluble at pH 4.8 and above. Most FD was soluble in water whose solution pH was 5.8 to 6.1. Only 0.9% remained insoluble. AD1, whose solution pH was 4.8–5.5, contained a bit more insoluble material or precipitate, 3.1%. AD2, whose solution pH was 3.2 to 3.9, contained even more insoluble material or precipitate, 9.4%. When the water extracts of FD and AD1 were acidified, precipitate formed (8.3 to 8.5%). The total precipitate of FD (9.4%) or AD1 (11.4%) was comparable to that of AD2 (9.7%). The % weight of the acid supernate from the first extract of freeze dried No.5(5)E-A or FD was 78.4%, which accounted for the balance of the material.

The first water extract and the precipitate of FD, and the acid supernate and the acid precipitate of the first water extract of FD were tested for anti-HIV activity. The results are shown in Table 10, which clearly indicated that the active component of FD or freeze-dried No.5(5)E-A was originally soluble in water and precipitable by acid. The main activity of FD was in the water extract (89% suppression on day 3 and 96% suppression on day 4 at 0.3 mg/mL) and not in the precipitate (13% suppression on both day 3 and day 4 at 0.3 mg/mL). The main activity of the water extract, in turn, was in the acid precipitate (97% suppression on day 3 and 98% suppression on day 4 at 0.3 mg/mL) and not in the acid supernate (4% suppression on day 3 and 22% suppression on day 4 at 0.3 mg/mL). The cytotoxic factor of the water extract (cytotoxicity: 75% of control at 0.3 mg/mL) apparently remained soluble in acid (cytotoxicity: 60% of control at 0.3 mg/mL) and was separable from the active acid precipitate (cytotoxicity: 90% of control at 0.3 mg/mL).

TABLE 10

Anti-HIV Activities Of Freeze Dried No. 5(5)E-A (FD) Fractions

| FD Fractions | Test Level % Weight | (mg/mL) | Toxicity* | Anti-HIV Activity** Day 3 | Day 4 |
|---|---|---|---|---|---|
| 1st Water Extract | 86.8% | 0.3 | 75% | 89% | 96% |
| Water Precipitate | 0.9% | 0.3 | 90% | 13% | 13% |
| 1st Water Extract HCl Supernate | 78.4% | 0.3 | 60% | 4% | 22% |
| 1st Water Extract HCl Precipitate | 8.5% | 0.3 | 90% | 97% | 98% |

*Toxicity in % of control proliferation.
**Activity in % suppression of HTV proliferation based on viral protein p24 level.

It was therefore hypothesized that the active component of the freeze dried No.5(5)E-A was essentially the same as that of the air dried No.5(5)E-A, and both were insoluble in acid. When No.5(5)E-A was freeze-dried, the active component remained soluble in water and became insoluble when the solution was acidified. When No.5(5)E-A was air dried, part or all of the active component was acidified and became insoluble, as in the case of AD1 and AD2. The source of acid was the HCl vapor from the acidic ethanol/water fractions, since the water and ethanol eluates (A and B) were air dried along with the acidic ethanol/water eluates (C and D) in the same hood.

To verify the hypothesis, the active water precipitate of AD2 was redissolved in a neutral and a basic solution and reprecipitated with acid. Thus, two 50-mg samples of the precipitate were each dissolved in 40 mL of PBS buffer a neutral (pH 7.2) or a basic 1% NH$_4$OH solution (pH 10.4). The dissolution of the sample was slow in the PBS buffer and rapid in the 1% ammonium hydroxide solution. Both samples were not completely solubilized even after being stored overnight in a refrigerator. The solutions were then centrifuged at 1,500 to 2,000 rpm for 40 minutes to separate the soluble from the insoluble. Each supernate was filtered through a 0.45-μm filter. Each brown precipitate was washed with 10 mL of its respective solvent and then 10 mL of water. The washes were separated by centrifuge at 2,000 rpm for 20 minutes and were discarded. Each washed precipitate and a 4.00 mL aliquot of each filtered supernate were nitrogen-dried and weighed. A 4.00 mL PBS buffer was also dried concurrently for solvent blank correction of the PBS supernate.

Two 17.0 mL aliquots of each of the supernates were pipetted into separate 50-mL centrifuge tubes. One aliquot was acidified by titration with 1% HCl until a precipitate formed. The other was acidified by titration with 1% acetic acid first and then with 1% HCl until it formed a precipitate. Titration with 1% acetic acid alone was insufficient to bring down the solution pH low enough to form precipitate. The solution pH titrated with 1% acetic acid leveled off at a pH of about 3.4 to 3.8 with no visible precipitate. Addition of 1% HCl was needed to bring the solution pH lower to around 1.5 to 1.8 to form precipitate. Visible precipitate began to form at solution pH around 2.2 to 2.5. When the supernates were titrated with 1% HCl, the solution pH's were lowered to 1.4 and 1.5 and precipitates formed. Precipitate began to form at pH around 2.3 for PBS supernate and around 3.3 for NH$_4$OH supernate titrated with HCl.

The acid supernate was separated from the acid precipitate by centrifuge at 2,000 rpm for 20 minutes. Each acid supernate (AS) was filtered through a 0.45-μm filter and nitrogen dried. Each acid precipitate (AP) was washed with 5 mL of 1% HCl once and nitrogen dried. The PBS supernate and precipitate, the acid (HCl) supernate and precipitate of the PBS supernate, and the acid (HCl) precipitate of the NH$_4$OH supernate were tested for anti-HIV activities. The results are shown in Table 11.

TABLE 11

Anti-HIV Activities Of Fractions Of The Active Air Dried No. 5(5)E-A Water Insoluble Fraction (AD2-WI)

| AD2-WI Fractions | % Weight | Test Level (mg/mL) | Toxicity* | Anti-Hiv Activity** Day 3 | Day 4 |
|---|---|---|---|---|---|
| PBS Supernate | 72.3% | 0.3 | 100% | 94% | 98% |
| PBS Precipitate | 28.9% | 0.3 | 74% | 26% | 34% |
| PBS Supernate HCl Supernate | 47.9% | 0.3 | 50% | 60% | 65% |
| PBS Supernate HCl Precipitate | 52.8% | 0.3 | 100% | 83% | 92% |
| NH$_4$OH Supernate HCl Precipitate | 50.2% | 0.3 | 92% | 93% | 97% |

*Toxicity in % of control proliferation.
**Activity in % suppression of HIV proliferation based on viral protein p24 level.

The results clearly evidence that the active component of AD2-WI is soluble in PBS at pH 7.2 and 1% NH$_4$OH solution at pH 10.4 and is precipitable by acid, such as HCl. The PBS supernate of AD2-WI is very active (94% suppression on day 3 and 98% suppression on day 4 at 0.3 mg/mL) while the PBS precipitate is marginally active (26% suppression on day 3 and 34% suppression on day 4 at 0.3 mg/mL). This is consistent with the observed activity of the AD2-WI whose active component had to be solubilized in the neutral cell culture medium for the anti-HIV assay.

The active component of AD2-WI was reprecipitated with HCl. The HCl precipitate of the PBS supernate of AD2-WI was fairly active (83% suppression on day 3 and 92% suppression on day 4 at 0.3 mg/mL) while the HCl supernate was moderately active (60% suppression on day 3 and 65% suppression on day 4 at 0.3 mg/mL). The moderate activity of the HCl supernate may be partially due to the cytotoxicity (50% of control proliferation). The acid precipitability of the active component of AD2-WI was further confirmed by the HCl precipitate of the NH$_4$OH supernate of AD2-WI which was very active (93% suppression on day 3 and 97% suppression on day 4 at 0.3 mg/mL).

From this information, it can be concluded that the active component of No.5(5)E-A is soluble in neutral or basic solutions and precipitable by acids such as HCl. Acetic acid, which is only able to bring the solution pH down to around 3.4 to 3.8, is not strong enough to cause precipitation of the active component. That means the active component in its acid form is stronger than acetic acid and weaker than hydrochloric acid. When neutralized with a base, such as NH$_4$OH, the active insoluble acid becomes a water soluble salt, which is also active against HIV.

More of the active component was prepared by acid precipitation from the water eluate No.5(5)E-A "as is" or the water extracts of freeze dried No.5(5)E-A by titration with 1% HCl. The acid precipitate was washed with water and freeze dried. The freeze dried acid precipitate was further purified by dissolving in 0.1 N ammonium bicarbonate (NH$_4$HCO$_3$) and reprecipitating it with 1.5 times volume of 1% HCl in water. For example, a 520.8 mg sample was completely solubilized in 20 mL of 0.1 N NH$_4$HCO$_3$. The solution was centrifuged at 2,000 rpm for 22 min and the supernate was filtered through a 0.45-μm filter. An aliquot of the solution was diluted with 0.1 N NH$_4$HCO$_3$ to 20.0 mL at 18.7 mg/mL, which was then acidified with 30.0 mL 1% HCl in water and formed a dark brown fluffy suspension and precipitate. The acidified solution was centrifuged at 2,000 rpm for 22 minutes. The acid supernate was decanted and discarded. The acid precipitate was washed with 30 to 45 mL of 1% HCl in water six times. The acid washes were each separated from the precipitate by centrifuge at 2,000 rpm for 22 minutes and discarded. The once purified acid precipitate (AP1X) was freezed dried and tested for anti-HIV activity. The result showed that the AP1X of No.5(5)E-A remained active: 75% suppression on day 3 and 87% suppression on day 4 at 0.31 mg/mL. That is, the anti-HIV activity survived the purification process.

2. No.5(5)E-C

Since the active component of No.5(5)E-A was identified to be the one soluble in neutral and basic solutions and precipitable by HCl, it was logical to see whether the active component of No.5(5)E-C possessed similar characteristics.

The air-dried No.5(5)E-C contained two distinct colored solids, one brown and one dark brown to near black. A solubility test was conducted by mixing 1.1–1.2 mg of the sample in one (1) mL of each solvent tested. The air-dried No.5(5)E-C was insoluble in ethanol, isopropanol, acetone, acetonitrile, chloroform, and hexane. It was slightly soluble in methanol and partially soluble in water, 1% HCl in water, 1% HCl in ethanol, and 0.1% HCl in 10% ethanol/90% water. It was mostly solubilized in PBS, 0.1 N NH$_4$HCO$_3$, 1% NH$_4$OH, and 1% NaOH in water with a small amount of off-white suspension or precipitate. The solubility appeared to progressively increase with the solution pH from acidic to neutral to slightly basic, and then decrease in a strong base like 1% NaOH in water.

The one-mL solutions of air-dried No.5(5)E-C in water, PBS, 0.1 N NH$_4$HCO$_3$, 1% NH$_4$OH, and 1% NaOH were each 0.45-μm filtered and acidified with 1.5 mL 1% HCl in water. All acidified solutions became yellowish brown to brown solutions and formed brown fluffy precipitates, except the acidified water solution in which no precipitate was observed.

In addition, the one-mL solutions of the air dried No.5(5)E-C in 1% HCl/water and 1% HCl/ethanol were each 0.45-μm filtered and mixed with 1.5 mL 1% NaOH to make the solution alkaline. The purpose was to see if these solutions contained insoluble bases. The alkalinated 1% HCl/water solution became a yellow-clear solution and the alkalinated 1% HCl/ethanol solution became yellowish-brown to brown solution. Both formed some golden brown fluffy precipitate after overnight storage in a refrigerator. The brown one-mL solution of No.5(5)E-C in 0.1% HCl/10% ethanol/90% water was also alkalinated the same way but with 1.5 mL of 1% NH$_4$OH. The brown solution became a light yellow clear solution upon alkalination precipitate did not form after overnight refrigerated storage. The results indicate that acidic and basic substances may be separated from No.5(5)E-C by precipitation with a strong acid and a strong base, respectively.

An 100.4 mg air dried sample of No.5(5)E-C was dissolved in 20.0 mL 0.1 N NH$_4$HCO$_3$. The solution was centrifuged at 2,000 rpm for 20 min and the supernate was transferred into a separate 50-mL centrifuge tube. The precipitate was extracted with 15.0 mL 0.1 N NH$_4$HCO$_3$ two more times. The supernates were pooled (total 50 mL). The precipitate was washed one more time with 15 mL 0.1 N NH$_4$HCO$_3$. The wash was separated by centrifuge at 2,000 rpm for 30 min and discarded. The precipitate was transferred into a WISP glass vial with 1 to 2 mL of water, nitrogen dried, and weighed 0.5 mg after drying, or 0.5% of the air dried No.5(5)E-C starting material.

The supernate was filtered through a 0.45-μm filter. Two 20.0 mL aliquots of the filtered supernate were pipetted into two 50-mL centrifuge tubes. The first 20-mL aliquot was acidified with 30 mL 1% HCl in water and formed a fluffy precipitate. The second 20-mL aliquot was made alkaline with 30 mL 1% NaOH. The alkalinated solution remained clear and with no visible suspension or precipitate after overnight refrigerated storage. The alkalinated solution also remained clear after being centrifuged at 2,000 rpm for 30 minutes or concentrated from 50 mL to 14 mL and then centrifuged. Addition of an additional 20 mL 1 N NaOH, to assure that the solution was alkaline (pH 13.23 at 22.5° C.), did not produce any visible precipitate.

The acidified solution was centrifuged at 2,000 rpm for 30 minutes to separate the fluffy acid precipitate. The acid precipitate was washed with 20 mL 1% HCl in water three times. Each wash was separated by centrifuge at 2,000 rpm for 30 minutes and discarded. The washed acid precipitate was freeze dried, tested for anti-HIV activity, and found active: 76% suppression on both day 3 and day 4 at 0.3 mg/mL.

The air dried No.5(5)E-C was fractionated again by directly dissolving it in 1% HCl in water to prepare the acid precipitable active component. The acid supernate was made alkaline to prepare the base precipitable component. A 203.8 mg air dried No.5(5)E-C sample was dissolved in 20 mL 1% HCl in water by vortexing the suspension for one (1) minute three times. The acid soluble portion was separated from the acid insoluble by centrifuge at 2,000 rpm for 30 min. The acid supernate (reddish brown solution) was filtered through a 0.22-μm filter. A 2.00 mL aliquot of the acid supernate was nitrogen dried and weighed 12.2 mg, or 59.9% of the air dried No.5(5)E-C starting material. The remaining 18 mL of the acid supernate was alkalinated with 7.5 mL of 1 N NaOH. Precipitate formed after cooling in a refrigerator for about 5 minutes. The base precipitate was separated from the base supernate by centrifuge at 2,000 rpm for 60 minutes. The base supernate was filtered through a 0.22-μm filter and neutralized with 5.0 mL of 1% HCl in water to pH 3.7 (clear brown solution). A 3.00 mL aliquot of the neutralized base supernate was nitrogen dried and weighed 54.5 mg.

The acid insoluble fraction of air dried No.5(5)E-C was washed with 20 mL 1% HCl in water twice. The base precipitate was washed with 20 mL 1% NaOH once. The washed acid insoluble fraction and the base precipitate were freeze dried and weighed 66.6 mg and 18.6 mg, respectively, or 32.7% and 10.1% of the air dried No.5(5)E-C.

The dried acid insoluble fraction, acid soluble fraction, base precipitate, and neutralized base supernate were tested for anti-HIV activities along with the starting material, air dried No.5(5)E-C. The results are shown in Table 12, which also shows the % weight of each fraction of No.5(5)E-C.

TABLE 12

Anti-HIV Activities Of Air Dried No. 5(5)E-C Fractions

| No. 5(5)E-C Fractions | % Wt | Test Level (mg/mL) | Toxicity** | Anti-HIV Activity* Day 3 | Day 4 |
|---|---|---|---|---|---|
| No. 5(5)E-C | 100% | 0.31 | 89% | 78% | 76% |
| Acid Insoluble | 32.7% | 0.30 | 91% | 84% | 85% |
| Acid Soluble | 59.9% | 0.31 | 92% | 12% | 19% |

TABLE 12-continued

Anti-HIV Activities Of Air Dried No. 5(5)E-C Fractions

| No. 5(5)E-C Fractions | % Wt | Test Level (mg/mL) | Toxicity** | Anti-HIV Activity* Day 3 | Day 4 |
|---|---|---|---|---|---|
| Base Precipitate | 10.1% | 0.31 | 90% | 16% | 20% |
| Base Supernate*** | 57.9% | 0.30 | 99% | 12% | 10% |

*Activity in % suppression of HIV proliferation based on viral protein p24 level. The data were repeated results using sample solutions stored frozen for three months.
**Toxicity in % of control proliferation.
***Neutralized with 1% HCl in water to pH 3.7 and nitrogen dried. The % weight shown excluded NaCl. The test sample contained 19.5% of No. 5(5)E-C fraction.

The results clearly demonstrated that the acid insoluble fraction contained the main active component of the air-dried No.5(5)E-C. The acid insoluble fraction was fairly active: 84% suppression on day 3 and 85% suppression on day 4 at 0.30 mg/mL. The acid soluble fraction was only marginally active: 12% suppression on day 3 and 19% suppression on day 4 at 0.31 mg/mL. Both the base precipitate and base supernate of the acid soluble fraction of No.5(5)E-C were also marginally active: 12 to 16% on day 3 and 10 to 20% on day 4 at 0.30 to 0.31 mg/mL.

It is therefore concluded that the active component of No.5(5)E-C, like that of No.5(5)E-A, is also soluble in neutral to slightly basic solutions but insoluble in strong acid solutions.

3. No.5(5)E

Since the active components of both the main active C18-SPE-LC fractions A and C of No.5(5)E (Table 7) have similar solubility properties (soluble in neutral to basic solutions and precipitable in a strong acid), the main active components of No.5(5)E can thus be prepared by direct acid precipitation from the water extract of No.5(5). The acid precipitate can be further purified by redissolution in 0.1 N NH$_4$HCO$_3$ and reprecipitation with hydrochloric acid one or more times. The NH$_4$HCO$_3$ solution of the acid precipitate was filtered through a 0.22-μm or 0.45-μm filter once during one of the purification cycles to remove residual insoluble particles.

A six (6) times purified acid precipitate of No.5(5)E, or No.5(5)E-AP6X, was tested for anti-HIV activity and found to remain very active, 99% suppression on day 3 and 97% suppression on day 4 at 0.25 mg/mL, as shown in Table 13. Where, the anti-HIV activities of No.5(5) and Raw No.5(5)E are shown for comparison. The percent (%) yield of No.5 (5)E-AP6X from two determinations is also listed.

TABLE 13

Anti-HIV Activities Of Water Extractable (E), Acid Precipitable (AP), And Acid Soluble (AS) Fractions Of No.4(2), No.4(3), No.4(4), No.4(5), No.5(1), No.5(4), No.5(5), No.5(8), No.5(11), G, and H

| Sample | Lot | % Yield** | Test Level | Toxicity*** | Anti-HIV Activity* Day 3 | Day 4 |
|---|---|---|---|---|---|---|
| No.4(2) | 1 | 100% | 2.5 mg/mL | 74–84% | 92% | 94% |
| No.4(2)E | 1 | 23.7% | 0.5 mg/mL | 68% | 62% | 0% |
| No.4(2)E-AP | 1 | 0.39% | 0.1 mg/mL | 100% | 83% | 83% |
| No.4(2)E-AS | 1 | 23.3% | 0.25 mg/mL | 69–90% | 0% | 0% |
| No.4(3) | 1 | 100% | 2.5 mg/mL | 75–78% | 100% | 100% |
| No.4(3)E | 1 | 55.3% | 0.5 mg/mL | 92% | 97% | 89% |
| No.4(4) | 1 | 100% | 2.5 mg/mL | 74–100% | 100% | 100% |
| No.4(4)E | 1 | 22.0% | 0.5 mg/mL | 67% | 100% | 100% |
| No.4(4)E-AP | 1 | 2.1% | 0.1 mg/mL | 69% | 85% | 95% |
| No.4(4)E-AS | 1 | 19.9% | 0.25 mg/mL | 75–100% | 91% | 82% |
| No.4(5) | 1 | 100% | 2.5 mg/mL | 41–79% | 98% | 92% |
| No.4(5)E | 1 | 21.9% | 0.5 mg/mL | 97% | 57% | 5% |
| No.4(5)E-AP | 1 | 0.19% | 0.3 mg/mL | 86–94% | 86% | 80% |
| No.4(5)E-AS | 1 | 21.7% | 0.25 mg/mL | 91–96% | 4% | 1% |
| No.5(1) | 1 | 100% | 2.5 mg/mL | 98% | 73% | 50% |
| No.5(1)E | 1 | 17.4 ± 0.3% | 0.5 mg/mL | 100% | 37% | 0% |
| No.5(1)E-AP | 1 | 0.30% | 0.3 mg/mL | 85–94% | 62% | 74% |
| No.5(4) | 1 | 100% | 2.5 mg/mL | 64% | 100% | 100% |
| No.5(4)E | 1 | 12.8 ± 1.6% | 0.5 mg/mL | 85% | 52% | 0% |
| No.5(5) | 1 | 100% | 2.5 mg/mL | 80–84% | 93% | 93% |
| Raw No.5(5)E | 1 | 18.7 ± 2.8% | 1.0 mg/mL | 99% | 91% | 97% |
| No.5(5)E-AP6X | 2 | 1.6 ± 0.1% | 0.25 mg/mL | 63–98% | 99% | 97% |
| No.5(8) | 1 | 100% | 2.5 mg/mL | 32–59% | 100% | 100% |
| No.5(8)E | 1 | 22.3 ± 3.1% | 0.5 mg/mL | 69% | 2% | 24% |
| No.5(8)E-AP | 1 | 0.26% | 0.1 mg/mL | 100% | 45% | 61% |
| No.5(11) | 1 | 100% | 2.5 mg/mL | 100% | 92% | 74% |
| No.5(11)E | 1 | 53.8% | 2.0 mg/mL | 74–94% | 87% | 73% |
| No.5(11)-AP | 1 | 4.36% | 0.3 mg/mL | 73–100% | 91% | 87% |
| No.5(11)-AS | 1 | 49.4% | 0.5 mg/mL | 100% | 84% | 65% |
| GE-AP | 1 | 1.0% | 0.30 mg/mL | 33% | 100% | 100% |
| GE-AP6X | 1 | 0.50% | 0.25 mg/mL | 66–93% | 100% | 99% |

TABLE 13-continued

Anti-HIV Activities Of Water Extractable (E), Acid Precipitable (AP), And Acid Soluble (AS) Fractions Of No.4(2), No.4(3), No.4(4), No.4(5), No.5(1), No.5(4), No.5(5), No.5(8), No.5(11), G, and H

| Sample | Lot | % Yield** | Test Level | Toxicity*** | Anti-HIV Activity* Day 3 | Day 4 |
|---|---|---|---|---|---|---|
| HE-AP | 1 | — | 0.30 mg/mL | 83% | 85% | 88% |
| HE-AS | 1 | — | 0.25 mg/mL | 87–91% | 24% | 0% |
| HE-AP1X | 2 | 0.30 ± 0.06% | 0.25 mg/mL | 93–100% | 95% | 90% |

*Activity in % Suppresion of HIV proliferation based on viral protein p24 level.
**From single determinations, except those with ± standard deviations were from 2 to 3 determinations.
***Toxicity in % of control proliferation.

4. GE

The source plant G of No.5(5) was tested to see whether the same acid precipitable anti-HIV active component can be isolated directly from the plant. Dried plant G was purchased from a local herbal store in Taiwan. A 100.8 g sample was extracted "as is" with water twice by boiling the whole dried plant in 2,900 mL water for 75 to 76 minutes each time. The first (~500 mL after evaporation) and the second (~120 mL after evaporation) extracts were separated respectively from the residue by decantation and filtered through a Whatman No. 4 filter paper. The first extract was acidified with 400 mL 1% HCl in water and the second extract was acidified with 145 mL 1% HCl in water. Precipitate formed in both acidified extracts (pH 1.5 for the first and 1.4 for the second). The acid precipitate (dark near black solid) was separated from the acid supernate (dark reddish-brown solution) by centrifuge at 2,000 rpm for 30 minutes.

Part of the acid precipitate of the first extract was washed with about 30 mL 1% HCl in water; then the inside wall of the 50-mL centrifuge tube was rinsed with about 15 mL water. The acid wash and the water rinse were separated from the acid precipitate by centrifuge at 2,000 rpm for 30 minutes and discarded. The acid precipitate was nitrogen dried (GE-AP), tested for anti-HIV activity and found very active: 100% suppression on both day 3 and day 4 at 0.30 mg/mL (Table 13). However, the GE-AP is cytotoxic at this level, 33% of control, and needs to be further purified to reduce the cytotoxicity.

Additional extractions with boiling water were conducted with dried plant chips which were cut to approximately ≦1 cm long. The percent (%) of extractables from the dried plant chips determined from two lots of the plant were from 21 to 27%. The water extracts from the chipped samples were acidified with HCl to produce acid precipitates which were then purified up to six cycles of dissolution and precipitation as described above for No.5(5)E-AP6X. The six (6) times purified GE-AP6X was tested for anti-HIV activity and found as active as No.5(5)E-AP6X, as shown in Table 13. GE-AP6X exhibited 100% suppression of HIV proliferation on day 3 and 99% suppression on day 4 at 0.25 mg/mL, while No.5(5)E-AP6X exhibited 99% suppression on day 3 and 97% suppression on day 4 at the same level. Cytotoxicity test also showed close similarity between the two active components, 66–93% of control proliferation for GE-AP6X and 63–98% for No.5(5)E-AP6X at the same 0.25 mg/mL.

5. HE

Plant H (*Dichondra micrantha*) was originally thought to be the source plant of the single-herb herbal medicine No.5(5), since the plant has a Chinese trivial name the same as that of the herbal medicine No.5(5). See H. C. Chang, *Medicinal Herbs* II, Holiday Publishing Co., Taipei, Taiwan, R.O.C., 27 (1991). Plant H was thus subjected to the same water extraction and acid precipitation as for plant G described above.

Dried whole plants of *Dichondra micrantha* (H) were extracted with boiling water as that described above for the extraction of plant G. The water extract was filtered and acidified with HCl and a precipitate formed. The acid precipitate (HE-AP) and the acid supernate (HE-AS) were tested for anti-HIV activities. The results clearly demonstrate that the acid precipitate HE-AP is the active component of the plant H water extract, the same situation as that for plant G and No.5(5), as shown in Table 13.

The acid precipitate HE-AP exhibited good anti-HIV activity: 85% suppression on day 3 and 88% suppression on day 4 at 0.30 mg/mL. The acid supernate HE-AS was not active: 24% suppression on day 3 and 0% suppression on day 4 at 0.25 mg/mL. A one (1) time purified acid precipitate HE-AP1X from a second lot was also tested as active: 95% suppression on day 3 and 90% suppression on day 4 at 0.25 mg/mL (Table 13). The samples were not toxic at the test levels, 83% of control proliferation for HE-AP, 93 to 100% of control for HE-AP1X, and 87 to 91% of control for HE-AS.

6. No.4(2), No.4(3), No.4(4), No.4(5), No.5(1), No.5(4) and No.5(8)

Since the active components of No.5(5) and plants G and H are all extractable by water and precipitable by acid, it is logical to see whether the active components of the other anti-HIV active single-herb herbal medicines have similar properties. The active herbal medicines were therefore checked to see whether they contained acid precipitable components and, if they did, whether these components were active.

A 5.0 g sample of each single-herb herbal medicine No.4(2), No.4(3), No.4(4), No.4(5), No.5(1), No.5(4) and No.5(8) was extracted with about 40 mL water twice in a 50-mL plastic centrifuge tube. Each extract was separated from the insoluble material by centrifuge at 2,000 rpm for 40 to 120 minutes. The first and second extracts of each sample were combined and then filtered through a 0.22-μm filter. A 2.00 mL aliquot of each extract was nitrogen dried and weighed. The remaining extract of each sample was acidified with 10 mL 1% HCl in water. Precipitates formed in all acidified extracts, except those of No.4(3) and No.5(4). No precipitate formed in the acidified extract of No.4(3), even after prolonged (9 hrs) storage in a refrigerator and addition of 10 mL more 1% HCl in water. The acidified extract of No.5(4) showed only cloudiness and formed a trace precipitate after centrifuge at 2,000 rpm for 20 minutes.

Each acid precipitate was separated from its supernate by centrifuge at 2,000 rpm for 20 minutes. Each acid precipitate was washed with 5 mL 1% HCl in water. The acid wash was separated by centrifuge at 2,000 rpm for 20 minutes and discarded. Each acid precipitate was nitrogen dried and weighed.

Each acid supernate was combined with 10 mL more 1% HCl in water. After being stored for four (4) days at ambient temperature, precipitates formed again in various degrees in all further acidified supernates, except that of No.4(3). Each acid supernate was separated from the precipitate by centrifuge at 2,000 rpm for 80 minutes, filtered through a 0.22-$\mu$m filter, and air dried. Each dried acid supernate was redissolved in 0.1 N $NH_4HCO_3$, transferred into a WISP glass vial, and freeze dried.

The dried water extracts (E), acid precipitates (AP), and acid supernates (AS) of No.4(2), No.4(4) and No.4(5) were tested for anti-HIV activities. The water extracts (E) and acid precipitates (AP) of No.5(1) and No.5(8) were also tested. As No.4(3) did not have acid precipitate and No.5(4) had only a minute amount of acid precipitate (0.3 mg), only their water extracts (E) were tested for anti-HIV activities. The results are shown in Table 13.

The results show that the water extracts (E) of No.4(3) and No.4(4) remain very active: 97% suppression on day 3 and 89% suppression on day 4 for No.4(3)E and 100% suppression on both day 3 and day 4 for No.4(4)E at 0.5 mg/mL. The activities of the water extracts (E) of No.4(2), No.4(5), No.5(1), No.5(4) and No.5(8), however, were surprisingly low: 2 to 62% suppression on day 3 and 0 to 24% suppression on day 4 at the same test level 0.5 mg/mL. As a comparison, the original herbal medicine powders have moderate to very good activities: 73 to 100% suppression on day 3 and 50 to 100% suppression on day 4 at 2.5 mg/mL.

Even more surprising, all acid precipitates (AP) exhibited moderate to good anti-HIV activities: 83% suppression on both day 3 and day 4 for No.4(2)E-AP, 85% suppression on day 3 and 95% suppression on day 4 for No.4(4)E-AP, 86% suppression on day 3 and 80% suppression on day 4 for No.4(5)E-AP, 62% suppression on day 3 and 74% suppression on day 4 for No.5(1)E-AP, and 45% suppression on day 3 and 61% suppression on day 4 for No.5(8)E-AP at 0.1 to 0.3 mg/mL. The acid supernate (AS) of No.4(4)E was fairly active, 91% suppression on day 3 and 82% suppression on day 4 at 0.25 mg/mL. The acid supernates (AS) of No.4(2)E and No.4(5)E were practically inactive: 0 to 4% suppression on day 3 and 0 to 1% on day 4 at 0.25 mg/mL.

Since the water extracts (E) of No.4(2), No.4(5), No.5(1), No.5(4) and No.5(8) are much less active than their original powders and the acid precipitates (AP) of No.4(2), No.4(5), No.5(1) and No.5(8) are fairly active, it is therefore hypothesized that the majority of the active components of these powders may not have been effectively extracted into water (pH 4.0 to 5. 1). Adjustment of the solution pH to neutral or slightly alkaline is expected to help improve the extraction.

It is concluded that the active components of No.4(2) and No.4(5) are precipitable by acid. The active component of No.4(3) is soluble in both water and acid. No.4(4) contains two active components, one acid soluble and one acid precipitable. No.5(1) and No.5(8) contain acid precipitable active components.

7. No.5(11)

The single-herb components No.5(10) and No.5(11) were included in the herb mixture HHT888-5 for treating HBV carriers (See Example 3). Both No. 5(10) and No. 5(11) were not included in the earlier anti-EMuLV and anti-HIV screening tests to prevent their potential interference with the antiviral assays of HHT888-5.

The above discoveries show that all the acid precipitable components or acid precipitates isolated from the single-herb herbal medicines and medicinal plants No.4(2), No.4(4), No.4(5), No.5(l), No.5(5), No.5(8) and H are anti-HIV active. It is therefore projected that acid precipitable components or acid precipitates, if any, isolated from other herbal medicines or plants will also be anti-HIV active.

To test the hypothesis, the single-herb herbal medicines No.5(10) and No.5(11) are extracted with water and their water extracts are acidified with HCl to see if acid precipitates will form. A 90.4 g sample of No.5(10) was extracted with twenty (20) times water (1804 to 1808 mL) at ambient temperature twice, followed by extraction with 900 mL 0.1 N $NH_4HCO_3$ once. A 90.8 g sample of No.5(11) was extracted with ten (10) times water (908 mL) at ambient temperature twice, followed by extraction with 870 mL 0.1 N $NH_4HCO_3$ once. The extractions were conducted in a 2000-mL glass Erlenmeyer flask and stirred magnetically for one (1) hour to overnight. The extract was separated from the insoluble by centrifuge at 8,000 rpm for 40 minutes.

When 1.0 mL of extract was acidified with 1.5 mL of 1% HCl in water, the two water extracts and the $NH_4HCO_3$ extract of No.5(10) showed no visible precipitates even after overnight refrigerated storage. The first water extract of No.5(11) became brown and formed precipitate almost immediately. The second water extract of No.5(11) became light yellowish and slightly opaque, and formed a small amount of precipitate after overnight storage at ambient temperature. The $NH_4HCO_3$ extract of No.5(11) became nearly colorless and with white colloidal precipitate. It was predicted that No.5(11) and its acid precipitate were likely anti-HIV active.

A 10.0 mL aliquot of each extract was freeze dried and weighed. The total extractable of No.5(10) was 66.3%. That of No.5(11) was 53.8%. Most of the extractable of No.5(10) was extracted by the two water extractions which constituted 97.9% of the total extractable. Most of the extractable of No.5(11) was extracted in the first water extraction (93.5%). The second water extraction was necessary for No.5(10), which constituted 31.2% of the total extractable. For No.5 (11), the second water extraction and the $NH_4HCO_3$ extraction constituted only 5.4% and 1.1%, respectively.

The remaining 868 mL of the first water extract, 898 mL of the second water extract, and 828 mL of the $NH_4HCO_3$ extract of No.5(11) were acidified with 14.6, 14.6, and 13.4 mL of concentrated HCl (37%), respectively. The acidified first water extract formed precipitate almost immediately. The acidified 2nd water extract and $NH_4HCO_3$ extract became cloudy and formed precipitate after overnight refrigerated storage. The acid precipitate (AP) of each acidified extract was separated from its acid supernate (AS) by centrifuge at 2,000 rpm for 40 minutes. The acid supernates of the first and the second water extracts were pooled in a 2000-mL glass Erlenmeyer flask. A 200 mL sample of each of the acid supernates from the acidified water extracts and $NH_4HCO_3$ extract was centrifuged at 8,000 rpm for 40 minutes and filtered through a 0.22-$\mu$m filter. A 20.0 mL of each micro-filtered acid supernate was nitrogen dried, redissolved in water, and freeze dried.

The acid precipitates of No.5(11)E from the acidified first and second water extracts and the acidified $NH_4HCO_3$ extract were rinsed with about 20 to 40 mL water twice. The water rinses were separated by centrifuge at 2,000 rpm for 40 minutes and discarded. The acid precipitates were freeze dried and weighed. The percent (%) yield of the acid precipitate was 4.36% of No.5(11). Most (96.3%) of the acid precipitate was isolated from the original powder by the first water extraction.

No.5(10), No.5(11), the water extract of No.5(10) or No.5(10)E, the first water extract of No.5(11) or No.5(11)E, the acid precipitate from the acidified first water extract of No.5(11) or No.5(11)E-AP, and the acid supernate from the acidified pooled first and second water extracts of No.5(11) or No.5(11)E-AS were tested for anti-HIV activities. The results (Table 13) show that No.5(10) and its water extract No.5(10)E are essentially not active: 65% suppression on day 3 and 0% suppression on day 4 for No.5(10) at 2.5 mg/mL and 0% suppression on both day 3 and day 4 for No.5(10)E at 2.0 mg/mL. No.5(11), its water extract No.5(11)E, and the acid supernate No.5(11)E-AS are moderately active: 92% suppression on day 3 and 74% suppression on day 4 for No.5(11) at 2.5 mg/mL; 87% suppression on day 3 and 73% suppression on day 4 for No.5(11)E at 2.0 mg/mL; and 84% suppression on day 3 and 65% suppression on day 4 for No.5(11)E-AS at 0.5 mg/mL. The acid precipitate No.5(11)E-AP is again fairly active: 91% suppression on day 3 and 87% suppression on day 4 at 0.3 mg/mL.

The results show that No.5(11) contains two active components, one is soluble in acid and one is precipitable by acid. Both active components are extractable from No.5(11) by water. This supports an additional aspect of the invention, that being all acid precipitable components or acid precipitates from selected plants as recited in this application, and possibly any plant, are effective pharmaceutical agents.

EXAMPLE 10

Isolation of Active Components

Active components have been isolated from either commercial extract powders or the plants by extraction with water. Preferably, the amount of water to dried plant material can range from 5 to 10 times (v/w) and at least two extractions are conducted. The pH of the extraction solution is preferably adjusted with an alkaline solution, such as a NaOH, to neutral or slightly alkaline (7 to 8) to facilitate the extraction. The extraction may be conducted at either ambient temperature (commercial powders) or boiling (chipped or pulverized plants) for one hour or longer.

The soluble extract can be separated from the insoluble plant material by filtration (i.e., nylon screen and filter paper) or by centrifuge (2,000 to 8,000 rpm for 40 minutes or longer). The extract is then acidified with any strong acid, such as HCl (approximately 0.6% final concentration or solution pH $\leq 2$) to produce the active acid precipitate. The acid precipitate can be separated by centrifuge such as at 8,000 rpm for 40 minutes or longer. The precipitate can be purified by repetitive cycles of dissolution in neutral or alkaline solution such as 0.1 N $NH_4HCO_3$ and subsequent precipitation in acid. The insolubles can be removed by centrifuge (such as at 8,000 rpm for 40 minutes or longer) and/or microfiltration (such as through 0.2 to 0.45-$\mu m$ filter).

The purified acid precipitate can be freeze dried, nitrogen dried, or air dried. It can also be converted to ammonium salt by dissolving the acid in an ammonium solution such as ammonium bicarbonate or ammonium hydroxide solution which is then freeze dried or spray dried. The purified acid precipitate can also be converted to other salts, such as sodium salt, by dissolving the acid in a suitable solution, like $NaHCO_3$. The acid precipitate can also be separated from the matrix by C18 column chromatography.

Chemically related water extractable and acid precipitable anti-HIV active components were isolated from seven (7) of the anti-HIV active single-herb herbal medicines: No.4(2), No.4(3), No.4(5), No.5(1), No.5(5), No.5(8), No.5(11) and two (2) medicinal plants *Aeginetia indica* (G) and *Dichondra micrantha* (H) identified in Examples 5 and 6 by the water extraction and acid precipitation procedure described above.

As a specific example, No.4(2), No.4(3), No.4(4), No.4(5), No.5(1), No.5(4), No.5(5), No.5(8) and No.5(11) which were prepared according to Example 2 were extracted twice with water at ambient temperature (about 25° C.) at 8 to 10 mL of water per gram of sample (e.g., 5 g powder with 40 mL water or 50 g powder with 500 mL water or 100 g powder with 1000 mL water) each time. The water suspension was mixed to extract by either vortexing for one (1) minute, standing for ten (10) minutes and vortexing for one (1) minute; or stirring magnetically for fifteen (15) minutes or longer depending on the sample size and suspension volume. For example, the suspension containing 5 g powder in 40 mL water was vortexed for one (1) minute, stood for ten (10) minutes and vortexed again for one (1) minute during the extraction. The suspension containing 50 to 100 g powder in 500 to 1000 mL water was stirred magnetically for fifteen (15) minutes or longer during the extraction. The water extract was separated from the insoluble materials by centrifuge at 1,500 to 8,000 rpm for twenty (20) to forty (40) minutes and filtration through a filter such as Whatman No.4 filter paper.

The medicinal plants *Aeginetia indica* (G) and *Dichondra micrantha* (H), or the source plants of the herbal medicines No.5(5) and H, were washed with cold water, dried, comminuted, and extracted with boiling water as described above in Example 2. The water extracts were cooled to ambient temperature and separated from the insoluble plant materials by decantation and filtration through a nylon screen (1.3 by 1.5 mm openings), centrifuge at 1,500 to 8,000 rpm for twenty (20) to forty (40) minutes, and filtration again through a Whatman No.4 filter paper.

The water extracts were then acidified to form precipitates through the addition of hydrochloric acid to a pH of <2. Each acid precipitate was separated from the acid solution by centrifuge in plastic centrifuge tubes or bottles. Each acid precipitate was washed at least three times with water or 0.1 or 1% hydrochloric acid. Samples of the water extract, acid precipitate (acid insoluble component) and acid supernate (acid soluble component) of each of the samples were nitrogen dried, air dried or freeze dried. These samples were then subjected to further testing and characterization.

The purified acid precipitates No.5(5)E-AP1X, No.5(5)E-AP6X, GE-AP1X, GE-AP2X, GE-AP6X, HE-AP1X, HE-AP6X, No.4(2)E-AP1X, No.5(8)E-AP1X, No.5(11)E-AP1X, and their ammonium salts No.5(5)E-AP1X-NH$_4$, GE-AP2X-NH$_4$, HE-AP1X-NH$_4$, No. 5(8)E-AP1X-NH$_4$, No.5(11)E-AP1X-NH$_4$ and No.4(2)E-AP1X-NH$_4$ were thus prepared as described above. The nomenclature used herein and in the claims can be illustrated by the following: No.5(5)E-AP1X means single herb medicine No.5(5) derived from *Aeginetia indica* that was water extracted (E), acid precipitated (AP) and purified once (1X) by re-dissolution in neutral or alkaline solution and re-precipitation with acid to result in the final chemical entity designated No.5(5)E-APIX.

For example, No.5(5)E-AP1X-NH$_4$ was prepared by first washing 4.0 to 4.9 g No.5(5)E-AP1X in 50-mL centrifuge tubes, respectively, with about 40 mL water four times. The water washes were separated by centrifuge at 2,000 rpm for 40 minutes and discarded. The water washed AP1X's were freeze dried (total 11.4 g) and then dissolved in about 600 mL 0.1 to 0.2 N NH$_4$HCO$_3$. The solution was centrifuged at 2,000 rpm for 40 minutes and the supernate was filtered through a 0.45-$\mu$m filter under vacuum. The filtrate was freeze dried and thus was prepared No.5(5)E-AP1X-NH$_4$.

GE-AP2X-NH$_4$ was prepared by dissolving 690.8 mg GE-AP2X in 20.0 mL 0.2 N NH$_4$HCO$_3$. The solution was centrifuged at 8,000 rpm for 40 minutes. No precipitate was observed. The supernate was filtered through a 0.22-$\mu$m filter. The filtrate was freeze dried and thus was prepared GE-AP2X-NH$_4$.

The other samples were prepared in similar fashion.

EXAMPLE 11

Characterization of Active Components
1. No.5(5) Active Components
No.5(5)E-A-AP and No.5(5)E-C-AP were previously identified to be the active components of No.5(5). It appears that these compounds are homologous polymeric organic acids based on their solubilities, HPSEC, C18-SPE-LC, and elemental analyses. Both acids have similar properties, except the molecular weight distribution and retention on C18 column. Both acids are insoluble in acid aqueous solutions but become soluble as salts in neutral and basic aqueous solutions. They are stable to air, heat, acid, weak alkali, and common organic solvents.

Elemental analysis of a six times purified acid precipitate No.5(5)E-AP6X as shown in Table 14 shows a high carbon content (50.98%) and a low ash content (2.35%). This indicates that No.5(5)E-AP6X is an organic acid. The SEM (Scanning Electron Microscopy) x-ray surface elemental analysis of No.5(5)E-AP6X indicated the presence of carbon, oxygen, phosphorus, chlorine, and sulfur. No arsenic, lead, mercury or iron was detected. No.5(5)E-AP6X and its components No.5(5)E-A-AP and No.5(5)E-C-AP, however, are all insoluble in common organic solvents, including ethanol, isopropanol, acetone, acetonitrile, chloroform, and hexane. No.5(5)E-A-AP is also insoluble in methanol. This indicates that these active acid precipitates are not simple organic acids.

TABLE 14

Elemental Analysis And Ash Contents of Six Times Purified Acid Precipitates (AP6X) of No.5(5)E, GE and HE

| Sample | % C | % H | % N | % S | % Cl | % P | % Ash |
|---|---|---|---|---|---|---|---|
| No.5(5)E-AP6X | 50.98 | 4.92 | 3.69 | 0.14 | 4.69 | <0.05 | 2.35 |
| GE-AP6X | 46.47 | 5.32 | 5.19 | 1.21 | 4.80 | 0.98 | 0.60 |
| HE-AP6X | 54.69 | 5.20 | 3.52 | 0.66 | 4.22 | 1.18 | 1.99 |

All acid precipitates (AP) investigated are slightly soluble in water at a slow dissolution rate. All become more soluble and at a more rapid rate in a mixture of water and ethanol, such as water to ethanol at a ratio of 40 to 60 by volume. This indicates that the acid precipitates are of polymeric nature as supported by the HPSEC analysis.

TABLE 15

Anti-HIV Activities And % Weight Distribution Of HPSEC Fractions Of No. 5(5)E-A-APIX And No. 5(5)E-C-AP

| HPSEC Fraction | % Weight | Test Level (mg/mL)*** | Toxicity** | Anti-HIV Activity* Day 3 | Day 4 |
|---|---|---|---|---|---|
| No. 5(5)E-A-AP1X | 100% | 0.31 | 98% | 75% | 87% |
| No. 5(5)E-A-AP1X-F6 | 8.3% | 0.03 | 100% | 19% | 11% |
| No. 5(5)E-A-AP1X-F7 | 24.8% | 0.08 | 93% | 79% | 78% |
| No. 5(5)E-A-AP1X-F8 | 33.1% | 0.1 | 94% | 80% | 83% |
| No. 5(5)E-A-AP1X-F9 | 24.8% | 0.08 | 100% | 73% | 69% |
| No. 5(5)E-A-AP1X-F10 | 16.5% | 0.05 | 100% | 37% | 14% |
| No. 5(5)E-A-AP1X-F11 to F12 | 8.3% | 0.03 | 100% | 13% | 21% |
| No. 5(5)E-A-AP1X-F13 to F16 | 8.3% | 0.03 | 96% | 9% | 15% |
| No. 5(5)E-C-AP-F7 | 8.3% | 0.03 | 100% | 0% | 0% |
| No. 5(5)E-C-AP-F8 | 16.7% | 0.05 | 100% | 95% | 85% |
| No. 5(5)E-C-AP-F9 | 16.7% | 0.05 | 100% | 98% | 92% |
| No. 5(5)E-C-AP-F10 | 25.0% | 0.08 | 100% | 80% | 35% |

TABLE 15-continued

Anti-HIV Activities And % Weight Distribution Of HPSEC Fractions Of No. 5(5)E-A-AP1X And No. 5(5)E-C-AP

| HPSEC Fraction | % Weight | Test Level (mg/mL)*** | Toxicity** | Anti-HIV Activity* Day 3 | Day 4 |
|---|---|---|---|---|---|
| No. 5(5)E-C-AP-F1 1 to F12 | 16.7% | 0.05 | 100% | 59% | 8% |
| No. 5(5)E-C-AP-F13 to F16 | 16.7% | 0.05 | 100% | 50% | 0% |

*Activity in % suppression of HIV proliferation based on viral protein p24 level. Anti-HIV activity data of No. 5(5)E-A-AP1X were the repeated results using solutions stored frozen for three months.
**Toxicity in % of control proliferation.
***Test levels for the HPSEC fractions were equivalent to 0.30 mg/mL of the starting material.

The results clearly indicate that the main activity of No.5(5)E-A-AP1X spreads over three fractions, Fractions 7 to 9, and appears to peak at the mass peak Fraction 8 (80% suppression on day 3 and 83% suppression on day 4 at 0.1 mg/mL). The main activity of No.5(5)E-C-AP also spreads over three fractions, Fractions 8 to 10, and appears to peak at Fractions 8 and 9 (95 to 98% suppression on day 3 and 85 to 92% suppression on day 4 at 0.05 mg/mL. It should be noted that the mass of No.5(5)E-C-AP peaked at Fraction 10 which, however, was only marginally active, 80% suppression on day 3 and 35% suppression on day 4 at 0.08 mg/mL.

One HPSEC fraction, Fraction 8, of No.5(5)E-C-AP was found by ultrafiltration to contain oligomeric molecules of molecular weight between 1,000 and 3,000 dalton. Another HPSEC fraction, Fraction 9, was found to contain polymeric molecules of molecular weight greater than 3,000 dalton. Fraction 9 was more lipophilic than Fraction 8, because Fraction 9 contained larger molecules but eluted later than Fraction 8 on the HPSEC using 0.1 N $NH_4HCO_3$ as the mobile phase. Both were tested comparably active: 95% suppression on day 3 and 85% suppression on day 4 for Fraction 8 and 91 to 98% suppression on day 3 and 87 to 92% suppression on day 4 for Fraction 9 at 0.05 to 0.25 mg/mL. Furthermore, a twice chromatographically purified HPSEC Fraction 8 of No.5(5)E-C-AP exhibited a dose response against HIV proliferation and had an $IC_{50}$ (50% inhibition concentration) of 6 1 μg/mL on day 3 and 17 μg/mL on day 4. The results are shown in Table 16. As a comparison, the $IC_{50}$ of AZT was 3 ng/mL on day 3 and 21 ng/mL on day 4, and that of d4T was 32 nM on day 3 and 540 nM on day 4, when tested concurrently.

TABLE 16

Anti-HIV Activities Of HPSEC Fractions 8 And 9 Of No. 5(5)E-C-AP At Various Concentrations

| HPSEC Fraction | % Wt | Test Level (mg/mL) | Toxicity** | Anti-HIV Activity* Day 3 | Day 4 |
|---|---|---|---|---|---|
| Fraction 8 (Run 1) | 16.7% | 0.05 | 100% | 95% | 85% |
| Double chromatographically Purified Fraction 8 (Run 2) | 10.3% | 1.0 | 100% | 93% | 85% |
| | | 0.3 | 100% | 85% | 69% |
| | | 0.1 | 100% | 87% | 79% |
| | | 0.03 | 100% | 89% | 81% |
| | | 0.01 | 100% | 74% | 32% |

TABLE 16-continued

Anti-HIV Activities Of HPSEC Fractions 8 And 9 Of No. 5(5)E-C-AP At Various Concentrations

| HPSEC Fraction | % Wt | Test Level (mg/mL) | Toxicity** | Anti-HIV Activity* Day 3 | Day 4 |
|---|---|---|---|---|---|
| | | 0.003 | 100% | 19% | 0% |
| | | 0.001 | 91% | 3% | 5% |
| Fraction 9 (Run 1) | 16.7% | 0.05 | 100% | 98% | 92% |
| Fraction 9 (Run 2) | 23.6% | 0.25 | 80–82% | 91% | 87% |

*Activity in % suppression of HIV proliferation based on viral protein p24 level.
**Toxicity in % of control proliferation.

The melting points, if there are any, of No.5(5)E-APIX-$NH_4$ and its purified HPSEC Fraction 8 were determined to be higher than 400° C. This is highly unusual as most organic compounds have melting points of less than 300° C.

2. G and H Active Components

The active components of plants G and H behave similarly to that of No.5(5). Both are polymeric organic acids which are soluble in neutral and slightly basic aqueous solutions and precipitable by acid. Elemental analysis (Table 14 ) of six times purified acid precipitates of GE and HE shows that both contain high carbon contents (46.47 to 54.69%) and low ash contents (0.60 to 1.99%).

The molecular weights of the water extractable and acid precipitable active components of No.5(5), G and H were estimated by HPSEC analysis to be mostly between 1,000 and 12,000 dalton and, however, some were lower than 1,000 dalton.

3. No.4(2), No.4(3), No.4(4), No.4(5), No.5(1), No.5(8) and No.5(11) Active Components The active components of all samples tested active were soluble in the neutral cell culture medium. The active components of No.4(2), No.4(5), No.5(1), No.5(8) and No.5(11) are precipitable by acid, while that of No.4(3) is not. The active component of No.4(3) is soluble in both water and acid solution. The active component of No.4(4) is also soluble in water. However, part of the active component of No.4(4) is precipitable by acid and part is not.

The melting point, if there is any, of No.5(8)E-AP1X-$NH_4$ is higher than 400° C.

4. Anti-HIV Activity Dose Response And Toxicity

As described above, a twice chromatographically purified HPSEC Fraction 8 of No.5(5)E-C-AP exhibits a dose response activity against HIV proliferation as shown in Table 16 and has an $IC_{50}$ of 6 μg/mL on day 3 and 17 μg/mL on day 4. Table 17 shows the anti-HIV activity dose responses of the water extractable and acid precipitable active components No.5(5)E-AP1X-$NH_4$, GE-AP2X-$NH_4$, HE-AP1X-$NH_4$, No.5(8)E-AP1X-$NH_4$, No.5(11)E-AP1X-$NH_4$ and No.4(2)E-AP1X-$NH_4$ in their ammonium salt forms. The dose responses of AZT from two different runs are listed for comparison.

GE-AP2X-$NH_4$ was not tested at 0.5 mg/mL because of high cytotoxicity (35% of control proliferation) at this concentration. Its cytotoxicity persisted at lower levels: 34% of control proliferation at 0.25 mg/mL and 41% at 0.13 mg/mL. No.4(2)E-AP1X-$NH_4$ also exhibited high cytotoxicity (44% of control proliferation) at 0.5 mg/mL, but became much less cytotoxic at lower levels: 72% of control proliferation at 0.25 mg/mL and 100% (not cytotoxic) at 0.13 mg/mL.

The acute toxicity of No.5(5)E-AP1X-$NH_4$ was investigated. Mice were used to determine acute toxicity and the compound was found not toxic even at a dose of 5,000 mg of the test substance per kilogram of the body weight (fed orally—bolus administration). Four groups of ten (10) male ICR mice (weighing 18 to 21 grams each) per group were used for the acute toxicity test. None of the forty mice were dead seventy two (72) hours after oral administration. The $LD_{50}$ of No.5(5)E-AP1X-$NH_4$ is therefore greater than 5,000 mg/kg (po, mice, 72 hours). Furthermore, tests for effects of No.5(5)E-APIX-$NH_4$ at 5,000 mg/kg on the central nervous system such as reflex depression, behavior depression, muscle relaxation, motor stimulation and autonomic nervous system of the test animals were all negative when observed one (1) hour and three (3) hours after the oral administration.

TABLE 17

Anti-HIV Activity Dose Responses Of The Water Extractable And Acid Precipitable Active Components Of No. 5(5), No. 5(8), No. 5(11), No. 4(2), G and H In Their Ammonium Salt Forms

| Active Component | Test Level (mg/mL) | Toxicity** | Anti-HIV Activity* Day 3 | Day 4 | $IC_{50}$ |
|---|---|---|---|---|---|
| No. 5(5)E-AP1X-$NH_4$ | 0.5 | >55% | 98% | 95% | 4.2 μg/mL |
| | 0.05 | | 81% | 75% | (day 3) |
| | 0.005 | | 53% | 13% | 16 μg/mL |
| | 0.0005 | | 1% | 0% | (day 4) |
| GE-AP2X-$NH_4$ | 0.05 | >41% | 100% | 96% | 7.2 μg/mL |
| | 0.005 | | 40% | 8% | (day 3) |
| | 0.0005 | | 6% | 0% | 20 μg/mL |
| | 0.00005 | | 3% | 0% | (day 4) |
| HE-AP1X-$NH_4$ | 0.5 | 100% | 92% | 95% | 8.7 μg/mL |
| | 0.05 | >89% | 87% | 95% | (day 3) |
| | 0.005 | | 33% | 23% | 8.3 μg/mL |
| | 0.0005 | | 4% | 0% | (day 4) |
| No. 5(8)E-AP1X-$NH_4$ | 0.5 | 77% | 99% | 100% | 9.5 μg/mL |
| | 0.05 | 100% | 91% | 92% | (day 3) |
| | 0.005 | | 30% | 16% | 10 μg/mL |
| | 0.0005 | | 0% | 0% | (day 4) |
| No. 5(11)E-AP1X-$NH_4$ | 0.5 | 78% | 98% | 99% | 11 μg/mL |
| | 0.05 | >99% | 91% | 92% | (day 3) |
| | 0.005 | | 26% | 11% | 13 μg/mL |
| | 0.0005 | | 12% | 0% | (day 4) |
| No. 4(2)E-AP1X-$NH_4$ | 0.5 | 44% | 100% | 100% | 14 μg/mL |
| | 0.05 | 100% | 88% | 83% | (day 3) |
| | 0.005 | | 20% | 0% | 19 μg/mL |
| | 0.0005 | | 2% | 0% | (day 4) |
| AZT | 0.1 μg/mL | — | 99–100% | 98–100% | 2.0 ng/mL |
| | 0.01 μg/mL | | 87–93% | 84% | (day 3) |
| | 0.001 μg/mL | | 23–53% | 0–26% | 4.2 ng/mL |
| | 0.0001 μg/mL | | 3–19% | 0% | (day 4) |

*Activity in % suppression of HIV proliferation based on viral protein p24 level.
**Toxicity in % of control proliferation.

No.5(5)E-AP1X-$NH_4$ is cytotoxic towards human PBLs in vitro at 1 mg/mL or higher: 55% of control proliferation at 1 mg/mL, 46% at 2 mg/mL, 11% at 5 mg/mL, and 0% at 10 and 20 mg/mL. No.5(5)E-AP6X exhibits a slight cytotoxicity (3% of control proliferation) at 0.5 mg/mL and are not toxic at 0.1 mg/mL and lower levels (98% of control proliferation at 0.1 mg/mL and 100% at 0.02 mg/mL). One fraction of the active component of No.5(5)E-AP, i.e., the chromatographically purified HPSEC Fraction 8 of No.5(5) E-C-AP, has been shown to be not cytotoxic: 100% of control proliferation even at 1.0 mg/mL (see Table 16).

5. Stability of Active Components

The water extractable and acid precipitable active components of No.5(5), No.5(8), No.5(11), No.4(2), G and H are stable to heat, air, strong acids and weak bases such as HCl and ammonium bicarbonate, ammonium hydroxide or sodium bicarbonate, and alcohols such as ethanol. They are active in either acid forms or salt forms such as ammonium or sodium salts.

No.5(5)E-AP1X-$NH_4$ remained very active (94% suppression on day 3 and 87% suppression on day 4 at 0.1 mg/mL) when tested after 15.6 months of storage at ambient temperature. GE-AP2X-NH$_4$ and HE-AP1X-NH$_4$ retained their activities (100% suppression on both day 3 and day 4 for GE-AP2X-NH$_4$ and 83% suppression on day 3 and 81% suppression on day 4 for HE-AP1X-NH$_4$ at 0.1 mg/mL) when tested after 13 months of storage at ambient temperature. No.5(8)E-AP1X-NH$_4$ and No.4(2)E-AP1X-NH$_4$ remained fairly active (85% suppression on day 3 and 81% suppression on day 4 for No.5(8)E-AP1X-NH$_4$ and 92% suppression on day 3 and 88% suppression on day 4 for No.4(2)E-AP1X-NH$_4$ at 0.1 mg/mL) when tested after 12.5 months of storage at ambient temperature. No.5(11)E-AP1X-NH$_4$ also remained fairly active (84% suppression on day 3 and 78% suppression on day 4 at 0.1 mg/mL) when tested after 12 months of storage at ambient temperature.

INDUSTRIAL APPLICABILITY

The instant invention is directed in part, to the discovery that specific medicinal plants or herbal medicines or their mixtures possess surprising antiviral activities without causing damage to the host cells. Further, the invention is directed to methods of treating humans and mammals infected with viruses such as HBV, HCV, or HIV. The data presented in this application clearly demonstrate that the identified compositions possess antiviral activity without toxicity to the host cells.

It can be concluded from the foregoing experiments that the herb mixture designated HHT888-4 is effective in treating HBV carriers and thus can be used to treat humans infected with HBV. The reduction of viral load in HBV patients and carriers will thus result in the prevention of HBV disease in the human and will also be effective in the treatment of humans exhibiting HBV disease. The clinical tests have also shown that the herb mixture HHT888-45 is effective in treating hepatitis C patients, and thus is expected to be effective in treating hepatitis B patients when administered alone or in combination with HHT888-5 or its antiviral single-herb components.

In addition, HHT888-5, HHT888-45, HHT888-54 and the individual anti-HIV active single-herb components have demonstrated efficacy in suppressing HIV proliferation in native human cells. Furthermore, HHT888-5, HHT888-45 and HHT888-54 have shown efficacy in treating patients infected with HBV and HCV. HHT888-4, HHT888-5, HHT888-45, HHT888-54, water extracts and active principles are also effective in treating humans infected with HIV, including HIV carriers and AIDS patients.

The therapeutic effects described herein may be accomplished through the administration of the herbal medicines "as is", or as teas, decoctions, beverages, candies or other confections, enteral liquid nutritional products such as infant formula and adult nutritional products, medical foods, nutritional supplements or neutraceuticals containing one or more of the herbal medicines or their extracts or the active principles. For pharmaceutical preparations, one or more of the antiviral herbal medicines or their extracts or active principles described above may be administered in unit dosage forms such as capsules, packets or tablets, with or without controlled-release coating(s).

The medical community is constantly in search of methods and products that will effectively treat viral infections, especially methods and products for treating humans infected with HBV, HCV, and HIV. The herb mixtures HHT888-4, HHT888-5, HHT888-45, HHT888-54, the single-herb components, their extracts, active principles and products containing these herbal compositions will be readily accepted by the medical community as an additional tool in the prevention and treatment of these devastating illnesses.

While certain representative embodiments have been described herein, it will be apparent to those skilled in the art that various changes and modifications may be made therein without departing from the spirit or scope of this invention.

We claim:

1. A composition of matter useful in the treatment of viral infections, said composition comprising:
    a) AEGINETIAE HERBA, prepared from an aqueous extract of the whole plant of at least one plant selected from the group consisting of *Aeginetia indica, Dichondra micrantha, Striga lutea* and *Dichondra repens;*
    b) BLECHNI RHIZOMA, prepared from at least one plant selected from the group consisting of *Blechnum orientale, Osmunda japonica, Woodwardia orientalis, Woodwardia unigemmata, Athyrium acrostichoides, Sphaeropteris lepifera, Cyrtomium falcatum* and Cyrtomium fortunei;
    c) LESPEDEZAE HERBA, prepared from at least one plant selected from the group consisting of *Lespedeza cuneata* and *Senecio scandens;*
    d) POLYGONI CUSPIDATI RHIZOMA, prepared from the rhizome of at least one plant selected from the group consisting of *Polygonum cuspidatum, Polygonum runcinatum* and *Polygonum reynoutria;*
    e) FORSYTHIAE FRUCTUS, prepared from the mature fruit of at least one plant selected from the group consisting of *Forsythia suspensa, Forsythia viridissima* and *Forsythia koreana;* and
    f) LIGUSTRI FRUCTUS, prepared from at least one plant selected from the group consisting of *Ligustrum lucidum* and *Ligustrum japonicum.*

2. The composition of matter according to claim 1 additionally comprising at least one member selected from the group consisting of:
    a) CIRSII RHIZOMA ET RADIX, prepared from the dried rhizoma or root or the whole plant of at least one plant selected from the group consisting of *Cirsium japonicum, Cirsium albescens* and *Cirsium japonicum var. australe;*
    b) BREEAE RADIX, prepared from the dried root of at least one plant selected from the group consisting of *Breea segetum* and *Breea setosum;*
    c) BAPHICACANTHIS RHIZOMA ET RADIX, prepared from the dried rhizoma and root of at least one plant selected from the group consisting of *Baphicacanthes cusia, Strobilanthes cusia, Isatis tinctoria, Isatis indigotica* and *Polygonum tinctorium;*
    d) PHELLODENDRI CORTEX, prepared from the cortex of at least one plant selected from the group consisting of *Phellodendron amurense, Phellodendron chinense, Phellodendron amurense var. sachalinense* and *Phellodendron wilsonii;* and
    e) BLETILLAE TUBER, prepared from the tuber of *Bletilla striata.*

3. A composition of matter useful in the treatment of viral infections, said composition comprising:

a) AEGINETIAE HERBA, prepared from the aqueous extract of the whole plant of at least one plant selected from the group consisting of *Aeginetia indica, Dichondra micrantha, Striga lutea* and *Dichondra repens;* b) LONICERAE FLOS, prepared from the flower bud of at least one plant selected from the group consisting of *Lonicera japonica* and *Lonicera confusa;* c) PRUNELLAE SPICA, prepared from the spica or whole plant of at least one plant selected from the group consisting of *Prunella vulgaris* and *Prunella vulgaris subsp. asiatica;* and d) LESPEDEZAE HERBA, prepared from at least one plant selected from the group consisting of *Lespedeza cuneata* and *Senecio scandens.*

4. The composition of matter according to claim 3, additionally comprising at least one member selected from the group consisting of:

a) SCUTELLARIAE, BARBATAE HERBA; and b) FORSYTHIAE FRUCTUS.

* * * * *